(12) United States Patent
Kandori et al.

(10) Patent No.: US 7,668,581 B2
(45) Date of Patent: Feb. 23, 2010

(54) BIOMAGNETIC MEASUREMENT APPARATUS

(75) Inventors: Akihiko Kandori, Tokyo (JP); Tsuyoshi Miyashita, Fuchu (JP); Kuniomi Ogata, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 866 days.

(21) Appl. No.: 11/183,985

(22) Filed: Jul. 19, 2005

(65) Prior Publication Data

US 2006/0079751 A1  Apr. 13, 2006

(30) Foreign Application Priority Data

Sep. 29, 2004  (JP) .............................. 2004-283010

(51) Int. Cl.
*A61B 5/00* (2006.01)
(52) U.S. Cl. ........................ 600/407; 600/408; 600/409; 324/232; 324/240; 324/244; 324/248
(58) Field of Classification Search ................ 600/407, 600/409, 425, 428, 481, 509, 512, 516, 517; 324/244, 248, 232, 240
See application file for complete search history.

(56) References Cited

U.S. PATENT DOCUMENTS

| 5,495,849 | A | 3/1996 | Hayashi et al. |
| 6,053,869 | A | 4/2000 | Kawagishi et al. |
| 6,187,032 | B1 | 2/2001 | Ohyu et al. |
| 6,230,037 | B1 * | 5/2001 | Tsukada et al. ............. 600/409 |
| 6,248,070 | B1 | 6/2001 | Kanda et al. |

(Continued)

FOREIGN PATENT DOCUMENTS

EP  0479208  4/1992

(Continued)

OTHER PUBLICATIONS

Jorg Schreiber, "A New Method for Choosing the Regularization Parameter in Time-Dependent Inverse Problems and Its Application to Magnetocardiography", IEEE Transactions on Magnetics, vol. 40, No. 2, Mar. 2004, pp. 1104-1107.

(Continued)

*Primary Examiner*—Brian Casler
*Assistant Examiner*—Baisakhi Roy
(74) *Attorney, Agent, or Firm*—Mattingly & Malur, P.C.

(57) ABSTRACT

A CAM (current arrow map) 71 and another CAM 72 are obtained from magnetocardiogram waveforms measured from both front and back sides of a subject using data at a point of time of an R-wave peak, then the coordinates of the CAM 72 are inverted in both x and y axis directions to obtain a CAM 73. The coordinates of each of the CAMs 71 and 73 are converted to polar coordinates to obtain CAMs 74 and 75 at both front and back sides of the subject. After that, the CAM 74 is adjusted to the CAM 76 in scale to obtain a CAM 76, and CAMs 74 and 76 are combined. Then, the CAM data at measuring points on each measuring-points-missing radius vector is inserted through an arithmetic processing by interpolation so that CAM data at every measuring point on a planispheric chart 77 are connected to each another consecutively.

22 Claims, 22 Drawing Sheets

U.S. PATENT DOCUMENTS

| | | | |
|---|---|---|---|
| 6,528,994 | B2 | 3/2003 | Suzuki et al. |
| 6,539,245 | B2* | 3/2003 | Tsukada et al. ............. 600/409 |
| 6,611,142 | B1 | 8/2003 | Jones et al. |
| 6,735,460 | B2* | 5/2004 | Tsukada et al. ............. 600/409 |
| 6,745,063 | B2* | 6/2004 | Tsukada et al. ............. 600/409 |
| 6,992,482 | B2* | 1/2006 | Shay et al. ................... 324/235 |
| 7,106,057 | B2 | 9/2006 | Matthews et al. ........... 324/248 |
| 7,123,952 | B2* | 10/2006 | Nakai et al. .................. 600/509 |
| 7,126,338 | B2* | 10/2006 | MacGregor et al. ......... 324/334 |
| 7,235,968 | B2* | 6/2007 | Popovic et al. .............. 324/247 |
| 7,403,809 | B2* | 7/2008 | Tsukada et al. ............. 600/409 |
| 2001/0009975 | A1 | 7/2001 | Tsukada et al. |
| 2002/0050815 | A1 | 5/2002 | Suzuki et al. |
| 2002/0115927 | A1* | 8/2002 | Tsukada et al. ............. 600/409 |

FOREIGN PATENT DOCUMENTS

| | | |
|---|---|---|
| JP | 2001-252253 | 9/2001 |
| JP | 2004-181041 | 7/2004 |

OTHER PUBLICATIONS

Part IV Visual Determination of Generators of the Magnetocardiogram, by Hosaka, et al. pp. 426-432. J. Electrocardiologoy, 9 (4) 1976.

"Noninvasive Diagnosis of Arrhythmic Foci by Using Magnetocardiograms-Method and Accuracy of Magneto-Anatomical Mapping System", Yamada, et al. vol. 16, No. 5, 2000. pp. 580-586.

"Construction of Tangential Vectors From Normal Cardiac Magnetic Field Components" by Miyashita, et al. pp. 520-523. 1998 IEEE.

Noninvasive Visualization of Multiple Simultaneously Activated Regions on Torso Magnetocardiographic Maps During Ventricular Depolarization, by Tsukada, et al. pp. 305-313. Journal of Electrocardiology vol. 32 No. 4. 1999.

"A Method of Detecting Myocardial Abnormality by using a current-ratio Map Calcuated form an Exercise-Induced Magnetocardiogram" by A. Kandori, et al. pp. 29-34. Medical & Biological Engineering & Computing 2001, vol. 39.

vol. 41, No. 1 (2003)25-34.

Three-Dimensional Automatic Image Warping in Cardiac SPECT. By A. Ella, et al. Nuclear Medicine Communications, 2000, 21, 1135-1146.

"Three-Dimensional Echocardiography for Quantitative left Ventricular Wall Motion Analysis" by Maehle, et al. vol. 11, No. 4, 1994. pp. 397-408.

A. Weis et al., "Dynamical MCG Mapping with an Atomic Vapor Magnetometer", Neurology and Clinical neurophysiology, Nov. 30, 2004, pp. 646-647.

* cited by examiner

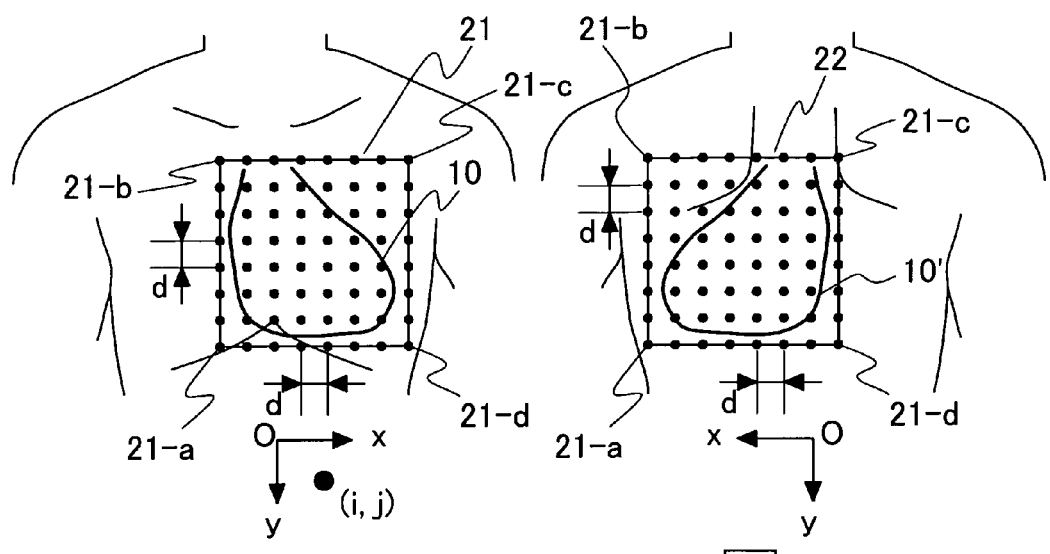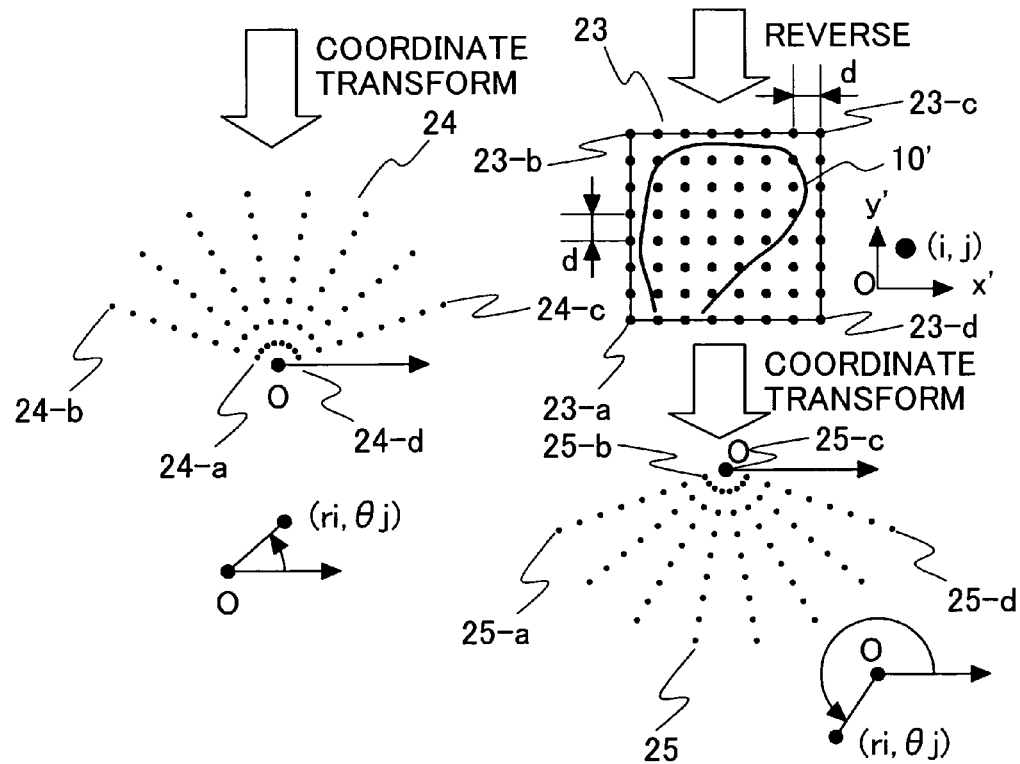

$Td(r, \theta)$

APEX $Td(r, \theta)$

APEX

BIOMAGNETIC MEASUREMENT APPARATUS

CLAIM OF PRIORITY

The present invention claims priority from Japanese application JP 2004-283010 filed on Sep. 29, 2004, the content of which is hereby incorporated by reference into this application.

FIELD OF THE INVENTION

The present invention relates to a biomagnetic measurement apparatus for measuring biomagnetic fields generated from living bodies with use of magnetometers.

FIELD OF THE INVENTION

In diagnoses of heart diseases such as arrhythmia, ischemic cardiac disease, etc., it is very important to visualize electro-physiological phenomena to occur in cardiac muscles. The biomagnetic measurement apparatus is one of such apparatuses for visualizing the electro-physiological phenomena. The biomagnetic measurement apparatus can measure very weak magnetocardiograms generated from respective hearts at multiple points in a noninvasive and non-contact manner and visualize the distribution of a current that flows in the cardiac muscles with use of measured magnetocardiogram data. (Hereinafter, a very weak magnetic field generated from a subject heart will be abbreviated as "a magnetocardiogram" and the waveform of the obtained magnetocardiogram will be described as a "magnetocardiogram waveform", and an illustration corresponding to the position of each magnetic field sensor used for measuring such magnetocardiogram data will be referred to as "a magnetocardiogram" or "magnetocardiogram map").

There is a report that cardiac current distribution is visualized with a current arrow map (hereinafter, to be abbreviated as "CAM") for denoting distribution of current vectors with both size and orientation of each of arrows (refer to the non-patent documents 1 and 2, for example). The CAM displays bio-current distribution with vectors on a two-dimensional plane obtained by differentiating a normal component of magnetocardiogram data measured at each measuring point. The CAM is calculated from magnetocardiogram data measured from both front and back sides of a subject to visualize how the electrical excitation is transmitted in the cardiac muscles of the whole subject heart (refer to the non-patent document 3, for example). There are also some methods for analyzing heart diseases according to such CAMs as described above, for example, visualizing how abnormal electric excitation is transmitted in subject heart muscles with use of time-series pictures of a CAM, identifying an ischemic region with the CAM in a ventricle depolarization process, etc. Effects of the use of such CAMs have been reported clinically (refer to the non-patent documents 4 and 5, for example).

In recent years, a report has been made for a method developed so that such a CAM is projected on a subject three-dimensional heart model created from the nuclear magnetic resonance imaging pictures, thereby displaying the current distribution in the cardiac muscles. This makes it easier to observe. (This method is disclosed in the non-patent document 6, for example.)

As known well, magnetocardiogram measurement is carried out with use of a biomagnetic measurement apparatus that uses SQUID (Superconducting Quantum Interference Device) magnetometers, which are superconducting devices.

There is also another report about magnetocardiogram measurement that uses LsOPM (laser pumped magnetometers)(as disclosed in the non-patent document 7, for example).

Also as known well, there is a cylindrical magnetic field shielding apparatus (as disclosed in the patent documents 1 and 2, for example) that disposes both of a subject measurement region and a cryostat having SQUID magnetometers therein.

There is still another well-known technique for displaying each planispherical map (bull's eye map) obtained by restoring three-dimensional information to its original two-dimensional information (refer to the non-patent documents 8 and 9, as well as the patent documents 3 to 5).

There are also various types of methods proposed for displaying data values obtained from a magnetocardiogram measured at each measuring point in which a plurality of magnetometers are disposed. For example, each of those methods displays equal magnetic-field-line charts for showing the strength of a magnetocardiogram with contour lines respectively, equivalent integral diagrams (as disclosed in the patent documents 6 and 7), current ratio maps (hereinafter to be referred to as a CRM respectively)(refer to the patent document 8), etc. The CRM is calculated in the following procedures of (a), (b), and (c). (a) A current vector is obtained at each measuring point from the magnetocardiogram data obtained from both before and after the subject's exercise stress, then the absolute value of the current vector at each measuring point is integrated in a predetermined time section to calculate integral current rates before and after the exercise stress and calculate integral current ratios before and after the calculated motive load at each measuring point. (b) The total sum of integral current flows at all the measuring points is obtained before and after the exercise stress to calculate the ratio between the integral current flows before and after the exercise stress as a normalization factor. (c) The ratio between integral current flows before and after the exercise stress calculated at each measuring point in (a) is normalized with the normalization factor.

The patent documents 9 and 10 disclose well-known methods, each of which displays changes of the size, phase, and intensity of a magnetic field vector with time at each measuring point at which the magnetocardiogram is measured as one graph without using many equivalent magnetic-field-line charts to obtain changes of electrical excitement in heart muscles with time.

[Patent document 1] Specification of U.S. Pat. No. 6,528,994
[Patent document 2] Official gazette of JP-A No. 136492/2002
[Patent document 3] Official gazette of JP-A No. 181041/2004
[Patent document 4] Official gazette of JP-A No. 155862/1999
[Patent document 5] Official gazette of JP-A No. 139917/2000
[Patent document 6] Official gazette of JP-A No. 305019/1998
[Patent document 7] Specification of U.S. Pat. No. 6,230,037
[Patent document 8] Official gazette of JP-A No. 252253/2001
[Patent document 9] Specification of U.S. Pat. No. 6,745,063
[Patent document 10] Official gazette of JP-A No. 238869/2002
[Non-patent document 1] H. Hosaka, et. al., "Visual determination of generators of the magnetocardiogram", J. Electrocardiol., vol. 9, pp. 426-432, 1976

[Non-patent document 2] T. Miyashita, et. al., "Construction of tangential vectors from normal cardiac magnetic field components", Proc. 20th Int. Conf. IEEE/EMBS (Hong Kong), pp. 520-523, 1998

[Non-patent document 3] K. Tsukada, et. al., "Noninvasive visualization of multiple simultaneously activated regions on torso magnetocardiographic maps during ventricular depolarization", J. Electrocardiol., vol. 32, no. 4, pp. 305-313, 1999

[Non-patent document 4] Y. Yamada, et. al., "Noninvasive diagnosis of arrhythmic foci by using magnetocardiogram-method and accuracy of magneto-anatomical mapping system—", J. Arrhythmia, vol. 16, no. 5, pp. 580-586, 2000

[Non-patent document 5] A. Kandori, et. al., "A method for detecting myocardial abnormality by using a current-ratio map calculated from an exercise-induced magnetocardiogram", Med. Biol. Eng. Comput., vol. 39, pp. 29-34, 2001

[Non-patent document 6] K. Ogata, et. al., "Visualization method of current distribute on in cardiac muscle using a heart model", Transactions of the Japanese society for medical and biological engineering, vol. 41, no. 1, pp. 25-33(2003)

[Non-patent document 7] A. Weis, et. al., "Dynamical MCG mapping with an atomic vapor magnetometer", BIOMAG 2004, Proceedings of the 14th International Conference on Biomagnetism, Boston, USA, pp. 646-647, 2004

[Non-patent document 8] A. Ella, et. al., "Three-Dimensional automatic imaging wrapping in cardiac SPECT", Nuclear medicine communicayions, 2000, Vol. 21, 1135-1146

[Non-patent document 9] "Three-Dimensional Echocardiography for Qunatitative Left Ventricular Wall Motion", ECHOCARDIOGRAPHY:A Jrnl. of CV Ultrasound & Allied Tech. Vo. 11, No. 4, 397-408(1994)

SUMMARY OF THE INVENTION

Conventionally, it has been just possible to observe a CAM that denotes current distribution in a subject heart, obtained from either the front side or back side of the subject heart at a time. In other words, it has been just possible to observe a CAM obtained at each measurement surface (front or back) where magnetic field sensors are disposed. Consequently, it has been impossible to observe the CAMs obtained from both of the measurement surfaces at a time, thereby it has been difficult to visually grasp the electrical activity in the whole heart muscles of the subject. This has been a conventional problem.

Under such circumstances, it is an object of the present invention to provide a biomagnetic measurement apparatus that can display a current distribution diagram, etc. of electrical excitement in the whole subject heart obtained by magnetic field measurement from two directions as a map on a planispheric chart.

The biomagnetic measurement of the present invention uses a planispheric chart (to display polar coordinates) to display magnetocardiogram data detected from both thoracic and back sides of a subject heart, a scalar value and/or vector value obtained from the magnetocardiogram data. And, changes of the planispheric chart with time are displayed on a display device.

Hereunder, typical configurations of the biomagnetic measurement apparatus of the present invention will be described.

(1) First Configuration

The biomagnetic measurement apparatus of the present invention includes a plurality of magnetic field sensors disposed two-dimensionally to detect a magnetic field generated from a subject, an arithmetic processing unit for collecting magnetic fields measured from first and second directions of the subject as first and second magnetic field data with the plurality of magnetic field sensors to process the first and second magnetic field data arithmetically, and a display device for displaying a result of the arithmetic processing.

The first direction is a direction from the thoracic (front) side of the subject and the second direction is a direction from the back side of the subject.

The arithmetic processing is executed to convert each of the positions of the plurality of magnetic field sensors when detecting the magnetic fields from the first and second directions to coordinates within a first range in which an oblique angle of polar coordinates, each represented by a radius vector r and an oblique angle $\theta$ is $0°<\theta<180°$ and within a second range in which the oblique angle $\theta$ of the polar coordinate is $180°<\theta<360°$ respectively, then set the first magnetic field data to correspond to the polar coordinates within the first range and set the second magnetic field data to correspond to the polar coordinates within the second range, thereby by combining data of the first and second magnetic fields to obtain data of the third magnetic field at the polar coordinates within the third range in which said oblique angle $\theta$ is $\theta=0°$ and $\theta=180°$.

(2) Second Configuration

The biomagnetic field measurement apparatus of the present invention includes a plurality of magnetic field sensors disposed two-dimensionally to detect magnetic fields generated from a subject, an arithmetic processing unit for collecting magnetic fields measured from first and second directions of the subject as first and second magnetic field data to process the first and second magnetic field data arithmetically, and a display device for displaying a result of the arithmetic processing.

The first direction is a direction from the thoracic (front) side of the subject and the second direction is a direction from the back side of the subject.

The arithmetic processing is executed to convert each of the positions of the plurality of magnetic field sensors when detecting the magnetic fields from the first and second directions to coordinates within a first range in which an oblique angle of polar coordinates having a common pole and, each of which is represented by a radius vector r and an oblique angle $\theta$ that is $0°<\theta<180°$ and within a second range in which the oblique angle $\theta$ of the polar coordinate is $180°<\theta<360°$ respectively, then set the first magnetic field data to correspond to the polar coordinates within the first range and set the second magnetic field data to correspond to the polar coordinates within the second range, thereby by combining data of the first and second magnetic fields to obtain data of the third magnetic field at the polar coordinates within the third range in which said oblique angle $\theta$ is $\theta=0°$ and $\theta=180°$, then set the first to third magnetic field data to each coordinate point on a planispheric chart that denoted by polar coordinates to calculate a scalar value and/or vector value from the magnetic field data at each coordinate point on the planispheric chart.

The planispheric chart for displaying distribution of the scalar value and/or vector value is thus displayed on the display device.

(3) Third Configuration

The biomagnetic field measurement apparatus of the present invention includes a plurality of magnetic field sensors disposed two-dimensionally to detect a magnetocardiogram generated from the heart of a subject, an arithmetic processing unit for collecting magnetocardiogram data measured from first and second directions of the subject as first and second magnetocardiogram data to process the first and second magnetic field data arithmetically, and a display device for displaying a result of the arithmetic processing.

The first direction is a direction from the thoracic (front) side of the subject and the second direction is a direction from the back side of the subject.

The arithmetic processing is executed to convert each of the positions of the plurality of magnetic field sensors when detecting the magnetic fields from the first and second directions to coordinates within a first range in which an oblique angle of polar coordinates having a common pole and, each of which is represented by a radius vector r and an oblique angle $\theta$ that is $0°<\theta<180°$ and within a second range in which the oblique angle $\theta$ of the polar coordinate is $180°<\theta<360°$ respectively, then set the first magnetic field data to correspond to the polar coordinates within the first range and set the second magnetic field data to correspond to the polar coordinates within the second range, thereby by combining data of the first and second magnetic fields to obtain data of the third magnetic field at the polar coordinates within the third range in which said oblique angle $\theta$ is $\theta=0°$ and $\theta=180°$, then set the first to third magnetic field data to correspond each coordinate point (assumed as $(r,\theta,t)$ while t denotes a point of time on the time axis of the subject magnetocardiogram waveform on a planispheric chart that denoted by polar coordinates to calculate a current vector (assumed as A $(r,\theta,t)$) from the magnetic field data corresponding to the coordinate point $(r,\theta,t)$.

The planispheric chart A $(r,\theta,t)$ is thus displayed on the display device.

(4) Fourth Configuration

The biomagnetic field measurement apparatus of the present invention includes a plurality of magnetic field sensors disposed two-dimensionally to detect a magnetocardiogram generated from the heart of a subject respectively, an arithmetic processing unit for collecting magnetic fields measured from first and second directions of the subject as first and second magnetocardiogram data to process the first and second magnetocardiogram data arithmetically, and a display device for displaying a result of the arithmetic processing.

The first direction is a direction from the thoracic (front) side of the subject and the second direction is a direction from the back side of the subject.

The arithmetic processing is executed to convert each of the positions of the plurality of magnetic field sensors when detecting the magnetic fields from the first and second directions to coordinates within a first range in which an oblique angle of polar coordinates, each represented by a radius vector r and an oblique angle $\theta$ is $0°<\theta<180°$ and within a second range in which the oblique angle $\theta$ of the polar coordinate is $180°<\theta<360°$ respectively, then set the first magnetic field data to correspond to the polar coordinates within the first range and set the second magnetic field data to correspond to the polar coordinates within the second range, thereby by combining data of the first and second magnetic fields to obtain data of the third magnetic field at the polar coordinates within the third range in which said oblique angle $\theta$ is $\theta=0°$ and $\theta=180°$.

(5) Fifth Configuration

The biomagnetic field measurement apparatus of the present invention includes a plurality of magnetic field sensors disposed two-dimensionally to detect a magnetocardiogram generated from the heart of a subject respectively, an arithmetic processing unit for collecting magnetic fields measured from first and second directions of the subject as first and second magnetocardiogram data to process the first and second magnetocardiogram data arithmetically, and a display device for displaying a result of the arithmetic processing.

The first direction is a direction from the thoracic (front) side of the subject and the second direction is a direction from the back side of the subject.

The arithmetic processing is executed to convert each of the positions of the plurality of magnetic field sensors when detecting the magnetic fields from the first and second directions to coordinates within a first range in which an oblique angle of polar coordinates having a common pole and each of which is represented by a radius vector r and an oblique angle $\theta$ is $0°<\theta<180°$ and within a second range in which the oblique angle $\theta$ of the polar coordinate is $180°<\theta<360°$ respectively, then set the first magnetocardiogram data or a value obtained from the first magnetic field data to correspond to the polar coordinates within the first range and set the second magnetic field data or a value obtained from the second magnetocardiogram data to correspond to the polar coordinates within the second range.

A planispheric chart on which the first magnetocardiogram data or value obtained from the first magnetocardiogram data, as well as the second magnetocardiogram data or value obtained from the second magnetocardiogram data are displayed at each coordinate point of polar coordinates is displayed on the display device.

Hereunder, a typical data analyzing method employed for the biomagnetic measurement apparatus of the present invention will be described.

The data analyzing method of the present invention analyzes first and second magnetocardiogram data generated from a subject heart, measured with a plurality of magnetic field sensors disposed two-dimensionally from first and second directions of the subject and collected into a memory.

The first direction is a direction from the thoracic (front) side of the subject and the second direction is a direction from the back side of the subject.

The arithmetic processing is executed to convert each of the positions of the plurality of magnetic field sensors when detecting the magnetic fields from the first and second directions to coordinates within a first range in which an oblique angle of polar coordinates having a common pole and, each of which is represented by a radius vector r and an oblique angle $\theta$ that is $0°<\theta<180°$ and within a second range in which the oblique angle $\theta$ of the polar coordinate is $180°<\theta<360°$ respectively, then set the first magnetic field data to correspond to the polar coordinates within the first range and set the second magnetic field data to correspond to the polar coordinates within the second range, thereby by combining data of the first and second magnetic fields to obtain data of the third magnetic field at the polar coordinates within the third range in which said oblique angle $\theta$ is $\theta=0°$ and $\theta=180°$, then set the first to third magnetic field data to correspond each coordinate point (assumed as $(r,\theta,t)$ while t denotes a point of time on the time axis of the subject magnetocardiogram waveform on a planispheric chart that denoted by polar coordinates to calculate a current vector (assumed as A $(r,\theta,t)$) from the magnetic field data corresponding to the coordinate point $(r,\theta,t)$.

Next, a description will be made for a configuration of the biomagnetic measurement apparatus of the present invention with respect to how to display magnetocardiogram data typically.

The magnetocardiogram data displaying method of the present invention displays the first and second magnetocardiogram data generated from the heart of a subject, which are measured with a plurality of magnetic field sensors disposed two-dimensionally from the first and second directions of the subject heart, then collected into a memory.

The first direction is a direction from the thoracic (front) side of the subject and the second direction is a direction from the back side of the subject.

The arithmetic processing is executed to convert each of the positions of the plurality of magnetic field sensors when detecting the magnetic fields from the first and second directions to coordinates within a first range in which an oblique angle of polar coordinates having a common pole and, each of which is represented by a radius vector r and an oblique angle θ that is 0°<θ<180° and within a second range in which the oblique angle θ of the polar coordinate is 180°<θ<360° respectively, then set the first magnetic field data to correspond to the polar coordinates within the first range and set the second magnetic field data to correspond to the polar coordinates within the second range, then set the first and second magnetocardiogram data to each coordinate point (assumed as (r,θ,t) while t denotes a point of time on the time axis of the magnetocardiogram waveform) on a planispheric chart represented by polar coordinates to display the planispheric chart for denoting distribution of a current vector (assumed as A (r,θ,t) obtained from the magnetocardiogram data corresponding to the (r,θ,t)).

According to the biomagnetic measurement apparatus of the present invention, a planispherical chart (displayed with polar coordinates) is used to display the heart's electrical excitation with a current distribution chart or the like, thereby the electrical activity of the whole heart can be observed at a time easily and the electrical excitation of the whole heart is found easily.

BRIEF DESCRIPTION OF THE DRAWINGS

FIG. 3 illustrates how measuring points of a magnetocardiogram are positioned and how their coordinates are converted;

DETAILED DESCRIPTION OF THE PREFERRED EMBODIMENTS

Figure 1:
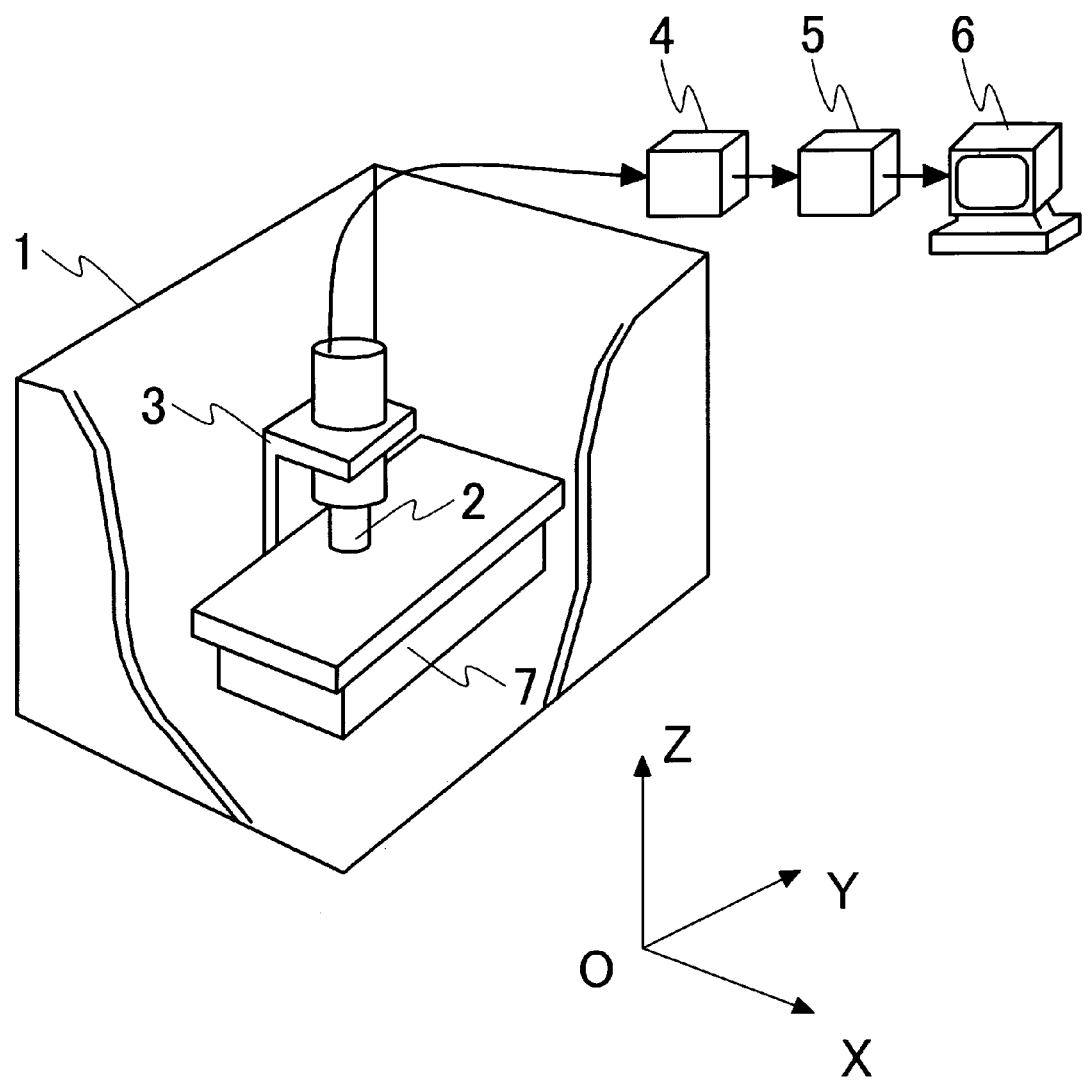
FIG. 1 illustrates a configuration of a biomagnetic measurement apparatus in an embodiment of the present invention.

FIG. 1 is a block diagram of a biomagnetic measurement apparatus in an embodiment of the present invention.

In a magnetically shielded room 1 for shielding the measurement apparatus from surrounding noise sources are disposed a bed 7 on which a subject is to be lie down, a cryostat 2 for preserving a coolant (liquid helium or liquid nitrogen) used to hold each SQUID magnetometer composed of a detecting coil and a SQUID in a superconductive state, and a gantry 3 for fastening the position of the cryostat 2. The SQUID magnetometer is driven by a driving circuit 4 disposed outside the magnetically shielded room 1 and its output is passed through an amplifier filter unit 5 and converted to digital magnetic-field data by an analog/digital conversion circuit built in a computer (arithmetic processing unit) 6, then stored in the computer 6. The computer 6 performs an arithmetic processing for the digital magnetic-field data as to be described below and the processing result is displayed on a display device of the computer 6 or another display device provided outside the computer 6.

Although SQUID magnetometers are employed as magnetic field sensors and the magnetically shielded room 1 is used in the configuration of the biomagnetic measurement apparatus shown in FIG. 1, the shielded room 1 may be omitted in case surrounding noise does not disturb the measurement so much. Instead of the shielded room 1 in which all of the bed 7, the cryostat 2, and the gantry 3, etc. are provided as shown in FIG. 1, the shielded room 1 may be configured cylindrically so that the cryostat 2 in which at least a measurement part and SQUID magnetometers are disposed is built in itself. Well-known LsOPMs may also be used as magnetic field sensors.

Figure 2:
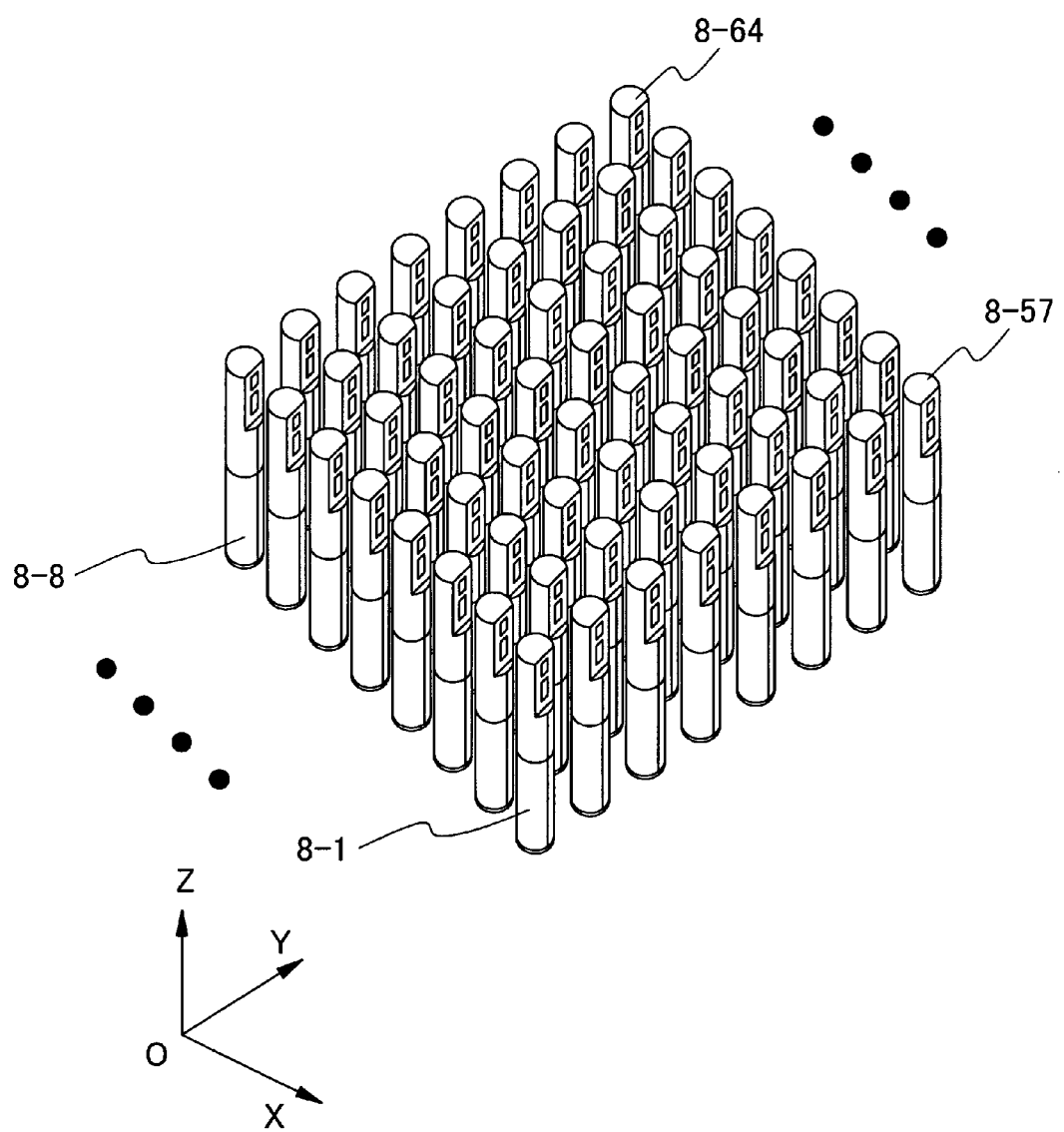
FIG. 2 illustrates how detecting coils are arranged in the biomagnetic measurement apparatus in the embodiment of the present invention.

FIG. 2 illustrates how to dispose detecting coils in the biomagnetic measurement apparatus in this embodiment of the present invention. In FIG. 2, the detecting coils 8 and the SQUID are united into one, so that each detecting coil 8 and a SQUID magnetometer are disposed at the same position. Thus, 64 detecting coils 8-1 to 8-64, each corresponding to its SQUID magnetometer, are disposed like an 8×8 matrix. In other words, each detecting coil of each of the 64 SQUID magnetometers, is disposed at a biomagnetic field measuring point, that is, at a node of the 8×8 square grid on an XY plane (magnetic measurement plane).

Each magnetic field sensor may be integrated with an assembly of a detecting coil 8 and a SQUID provided one on a substrate. The format of the disposed magnetic field sensors may not be limited only to the 8×8 square matrix; it may be an N×N square matrix (N=6, 9, 10, . . . ). The magnetic field sensors may also be disposed in a given format and at given intervals according to how the apparatus is to be used. In addition, the space of the region for disposing the magnetic field sensors is just required to cover the subject heart or the like from which biomagnetic fields such as magnetocardiograms are to be detected. The intervals of the magnetic field sensors to be disposed in this region are determined by taking the object space resolution into consideration.

In this embodiment of the present invention, plural detecting coils are disposed like a matrix, so that the current vector calculation is easy (the details will be described in detail). However, the current vector calculation method may be any of the minimum norm method, a method for calculating an inverse matrix such as a lead field or the like, etc. There is no need to dispose the detecting coils as shown in FIG. 2. For example, a plurality of SQUID magnetometers may be disposed two-dimensionally on a plane formed like any of a rectangular grid pattern, an oblique grid pattern, a concentric circle pattern, and a hexagonal pattern. The plurality of SQUID magnetometers may also be disposed two-dimensionally on an inner concave surface having a predetermined curvature after they are disposed like any of a rectangular grid pattern, an oblique grid pattern, a concentric circle pattern, and a hexagonal pattern. The above embodiment of the present invention can also apply to such disposition of the SQUID magnetometers.

Next, a description will be made for a planispheric chart A (r, θ, t) observable from the tip (apex cordis) in the lower portion of the subject heart with a map showing the state of the electrical excitation of the heart at both thoracic (front) and back sides of the subject in the above embodiment of the present invention. The A (r, θ, t) represents both of a current vector and a given vector value or scalar value.

In the embodiment of the present invention, the first magnetocardiogram data is measured from the thoracic surface and the second magnetocardiogram data is measured from the back side of the subject respectively in parallel to the surface of measurement by a plurality of magnetic field sensors. Each of the positions of the plurality of magnetic field sensors are converted to polar coordinates having a common pole and represented by a radius vector r and an oblique angle θ in the first range in which the oblique angle is 0°<θ<180° and within the second range in which the oblique angle θ is 180°<θ<360° respectively. Then, the first magnetic field data or value obtained from the first magnetocardiogram data is set to correspond to the polar coordinates within the first range and the second magnetic field data or value obtained from the second magnetocardiogram data is set to correspond to the polar coordinates within the second range. After that, a planispheric chart A (r, θ, t) at a point of time t is obtained by an arithmetic processing (to be described later with reference to FIGS. 3 through 13). The planispheric chart A displays the first magnetic field data or value obtained from the first magnetocardiogram data, as well as the second magnetic field data or value obtained from the second magnetocardiogram data at a converted polar coordinate point (r,θ) respectively.

In the following example, how to display various types of data obtained from a planispheric chart or data obtained from the planispheric chart with reference to each complete example of CAM.

Here, a B chart (θ, t) for representing changes of the A (r, θ, t) with time (to be described later with reference to FIGS. 13 through 16), a time-delay map Td (θ, t) (to be described later with reference to FIGS. 17 through 19), and a projected display of the Td (θ, t) on a three-dimensional heart model (to be described later with reference to FIGS. 20 and 21) will be picked up as examples of maps to be created from data of the planispheric chart A (r,θ,t).

In the following description, it is premised that the observer looks at a plane in the center between the two measurement surfaces (front side measuring position 21 and the back side measuring position 22 shown in the upper chart in FIG. 3A and the upper chart in FIG. 3B) and the planispheric chart A (r, θ, t) is observable from a vertical direction to a line for the connection between the positions of the reference numbers 21-*a* and 21-*d*, that is, from the tip (apex cordis) in the lower portion of the subject heart. It is also possible that the planispheric chart A (r, θ, t) is observable from any direction while the observer looks at the plane located in the center between the thoracic (front) side measurement position and the back side measurement position.

For example, as the given direction in (a), it is possible to select a direction vertical to any of the line connecting the positions of the reference numbers 21-*b* and 21-*c* or line connecting the positions of the reference numbers 21-*a* and 21-*b*, and the line connecting the positions of the reference numbers 21-*c* and 21-*d* shown in the upper charts shown in FIGS. 3A and 3B. In that case, it is just required to execute the procedures to be described in detail with reference to each drawing to be described later after correcting the setting of the origin of the coordinates (x, y) and its directions shown in the upper charts in FIGS. 3A and 3B. The description will be omitted here to avoid redundancy.

(b) When obtaining a planispheric chart A (r, θ, t) on which a subject heart can be observed from any of the directions other than the directions shown in the upper charts in FIGS. 3A and 3B, that is, from a given direction while the observer looks at an axis vertical to the subject thoracic surface, this given direction is determined as a new y axis direction and a new x axis direction is set vertically to the new y axis. Then, measuring points are set at the new coordinates (x, y) respectively in a new square grid pattern so that each of the sides of the square comes to be in parallel to both of the x and y axes and the region of the original square grid pattern with measuring points (as shown in the upper charts in FIG. 3A and FIG. 3B) is inscribed inside or circumscribed outside the square. For example, the new measuring points are disposed in an 8×8 pattern (generally, the grid pattern may be an N×N one).

The magnetocardiogram waveform at each measuring point of the new 8×8 grid pattern is obtained by interpolation or extrapolation from the magnetocardiogram waveform measured at the original 8×8 measuring points. The origin O (0,0) of the new coordinates (x, y), as to be described later, is set matching with the top left measuring point at a view from the thoracic surface. Even in this case (b), it is just required to execute the procedures to be described in detail with reference to each drawing according to the new coordinates (x, y). The description will be omitted here to avoid redundancy.

FIG. 3 is a chart for describing measuring points (positions of SQUID magnetometers) of a magnetocardiogram and conversion of coordinates in the above embodiment of the present invention. FIG. 3A shows a chart for describing how the SQUID magnetometers are disposed at the front side measuring position 21 and how the coordinates of those measuring points are to be converted while FIG. 3B shows a chart for describing how the SQUID magnetometers are disposed at the back side measuring position 21 and how the coordinates of those measuring points are to be converted.

In FIG. 3A, the SQUID magnetometers are disposed so as to face the thoracic (front) side and each magnetocardiogram is measured from the front side of the subject heart (anterior side). In FIG. 3B, the SQUID magnetometers are disposed so as to face the back side and each magnetocardiogram is measured from the back side of the subject heart (posterior side).

In the following description, the coordinate plane xy is assumed on the thoracic surface that is in parallel to the measuring position and the origin O (0,0) of the coordinates (x, y) is assumed at the position of the top left reference number 21-b (that is, a position matching with the top left measuring point at a view from the thoracic surface) while the forward directions of the x and y axes are those shown in the upper chart in FIG. 3A. Consequently, in the upper chart in FIG. 3B, the forward direction of the x axis comes to be opposite to that in the upper chart in FIG. 3A.

Also in the following description, as shown in FIG. 3, 64 detecting coils disposed like a square grid pattern shown in FIG. 2 are used to measure a magnetocardiogram with respect to each of the 64 channels related to the disposed positions of the detecting coils 8-1 to 8-64. Hereinafter, such an example will be described. The number of SQUID magnetometers (that is, the number of channels) to be used may not be 64.

As shown in FIG. 3A, while the subject lies down on the bed 7 with his/her face upward, the bottom surface of the cryostat 2 is disposed to face the thoracic surface of the subject and the 64 SQUID magnetometers are disposed on the xy surface. At that time, some of the 64 SQUID magnetometers are projected on the thoracic surface so that they are overlapped on at least part of the heart 10 at a view from the thoracic surface.

As shown in FIG. 3B, while the subject lies down on the bed 7 with his/her face downward, the bottom surface of the cryostat 2 is disposed to face the subject back side and the 64 SQUID magnetometers are disposed on the xy surface. At that time, some of the 64 SQUID magnetometers are projected on the back side so that they are overlapped on at least part of the heart 10 at a view from the back side.

At first, a description will be made for how the rectangular coordinates (x, y) of the measuring points at the front side measuring position 21 are to be converted. As shown in FIG. 3A, the SQUID magnetometers are disposed in both x and y directions at equal intervals d. Reference numbers 21-a, 21-b, 21-c, and 21-d denote positions of the SQUID magnetometers disposed at the four corners. In the upper chart in FIG. 3A, the rectangular coordinates (xi, yi) of each SQUID magnetometer disposed on the i-row (x direction) and the j-th column (y direction), as shown in the lower chart in FIG. 3A, are converted to polar coordinates (ri,θj) for which the pole is denoted by O, the radial diameter is denoted by ri, and the deflection angle assuming the forward of the x axis in the upper chart in FIG. 3A as a base line is assumed as θj. In case the SQUID magnetometers are disposed in an N×N pattern (N: positive integer) (in this example, N=8, 8×8 matrix), the rectangular coordinates (xi, yi) are converted to polar coordinates (ri,θj) in (expression 1) and (expression 2). In the (expression 1) and the (expression 2), it is assumed that i=1, 2, ..., N and j=1, 2, ..., N, and Δθ=180°/(N+1) is satisfied. The front measuring position 21 that uses rectangular xy coordinates shown in the upper chart in FIG. 3A is converted to a front side measuring position 24 that uses polar coordinates (r,θ) shown in the lower chart in FIG. 3A. The front side measuring position 24 that uses polar coordinates (r,θ) forms a fan-like pattern on the condition of 0°<θ<180°.

$$ri = i \times d \quad \text{(Expression 1)}$$

$$\theta j = (N-j+1) \times \Delta\theta \quad \text{(Expression 2)}$$

In other words, in the upper chart shown in FIG. 3A, the position of the reference number 21-a is moved to the position of the first row and the first column, the position of the reference number 21-c is moved to the position of the eighth row and the eighth column, the positions of the SQUID magnetometers on the i-th row in the upper chart in FIG. 3A are on a semi-circle having a radius ri=i×d and disposed at a position having a deflection angle θj=(N−j+1)×Δθ (j=1, 2, ..., N) at equal angular intervals Δθ from the base line. The SQUID magnetometers positioned on the j-th column are disposed at positions of a radius vector ri=i×d (j=1, 2, ..., N) at a deflection angle θj=(N−j+1).

The SQUID magnetometers positioned at the first row between the positions of the reference numbers 21-a and 21-d in FIG. 3A come to be disposed on the innermost semi-circle when they are represented by polar coordinates as shown in the lower chart in FIG. 3A while the SQUID magnetometers positioned at the eighth row between the positions of the reference numbers 21-b and 21-c shown in the upper chart in FIG. 3A come to be disposed on the outermost semi-circle when are represented by polar coordinates as shown in the lower chart in FIG. 3A. More concretely, in both of the upper and lower charts in FIG. 3A, the position of the reference number 21-b corresponds to the position of the reference 24-b, the position of the reference number 21-c corresponds to the position of the reference 24-c, the position of the reference number 21-a corresponds to the position of the reference 24-a, and the position of the reference number 21-d corresponds to the position of the reference 24-d respectively.

Next, a description will be made for how to convert the rectangular coordinates (x, y) of each measuring point at the back side measuring position 22. The origin of the plurality of SQUID magnetometers disposed at the back side measuring position 22 should preferably match with the origin O of the plurality of SQUID magnetometers disposed at the front side measuring position 21. For example, the origin O of the plurality of SQUID magnetometers disposed at the back side measuring position 22 is set at a back side position at which the origin O (for example, processus xiphoideus) of the plurality of SQUID magnetometers disposed on the front side measuring position 21 is projected. Otherwise, an equal magnetic field curve that connects points having the same R waveform signal peak intensity of each magnetocardiogram waveform measured by each SQUID magnetometer from the back side is obtained, then this equal magnetic field curve is inverted in the x axis direction to obtain another equal magnetic field curve.

After that, those obtained equal magnetic field curves are compared with an equal magnetic field curve that connects points having the same signal intensity of the R waveform of the magnetocardiogram waveform obtained by each SQUID magnetometer from the front side of the subject. In other words, the equal magnetic field curve obtained from the back side measured data is moved in parallel to the directions of both x and y axes so that the equal magnetic field curve obtained from the back side measured data matches mostly with the equal magnetic field curve obtained from the front side (reference) measured data. Then, the equal magnetic field curve obtained from the back side measured data is moved parallelly to the matching position. The origins O of the front and back side measuring positions 21 and 22 are then aligned to each other.

The SQUID magnetometers as shown in the upper chart in FIG. 3B are disposed at equal intervals d in the directions of both x and y axes just like the rectangular coordinates (x, y) of the measuring points at the front side measuring position 21 as shown in the upper chart in FIG. 3A. The reference numbers 21-*a* to 21-*d* denote the positions of the SQUID magnetometers disposed at the four corners. At first, the rectangular coordinates (x, y) of the measuring points shown in the upper chart in FIG. 3B are inverted in the directions of both x and y directions to obtain the back side measuring position 23 (shown in the middle chart in FIG. 3B) of the rectangular coordinates (x', y'). More concretely, in the upper and middle charts in FIG. 3B, the position of the reference number 21-*b* corresponds to the position of the reference number 23-*d*, the position of the reference number 21-*c* corresponds to the position of the reference number 23-*a*, the position of the reference number 21-*a* corresponds to the position of the reference number 23-*c*, and the position of the reference number 21-*d* corresponds to the position of the reference number 23-*b* respectively.

In the middle chart in FIG. 3B, while the position of the reference number 23-*b* is set at a position of the first row and the first column and the position of the reference number 23-*d* is set at a position of the eighth row and the eighth column, the rectangular coordinates (x'i, y'j) of the SQUID magnetometer at a position of the i-th row (x' axis direction) and the j-th column (y' axis direction) are converted to the polar coordinates (ri, θj) having a pole O, a radius vector ri, and a deflection angle θj from the base line that is the x' axis shown in the middle chart in FIG. 3B. In case the SQUID magnetometers are disposed in an N×N pattern (assumed to be N=8, an 8×8 matrix in this example), the rectangular coordinates (x'i, y'j) are converted to polar coordinates (ri, θj) according to the (expression 1) and the (expression 2). In the (expression 1) and the (expression 2), i=1, 2, . . . , N, j=1, 2, . . . , N, Δθ=180'/(N+1) is satisfied. The back side measuring position 23 of the rectangular coordinates (x', y') shown in the middle chart in FIG. 3B is converted to the back side measuring position 25 of the polar coordinates (r,θ) shown in the lower chart in FIG. 3B. The back side measuring position 25 of the polar coordinates (r,θ) is formed in a fan-like pattern on the condition of 180°<θ<360°. The coordinates (r,θ) in the lower chart in FIG. 3A and the polar coordinates (r,θ) in the lower chart in FIG. 3B have a common pole.

In other words, the positions of the SQUID magnetometers on the ii-th row shown in the middle chart in FIG. 3B is positioned on a half circle having a radius ri=i×d and disposed at a position having a deflection angle θj=180°+j×Δθ (j=1, 2, . . . , N) and at equal angular intervals Δθ from the base line. The SQUID magnetometers on the j-th column are disposed at a position having a radius vector ri=i×d (j=1, 2, . . . , N) at a deflection angle θj=180°+j+Δθ.

The SQUID magnetometers disposed on the first row between the positions of the reference numbers 23-*b* and 23-*c* shown in the middle chart in FIG. 3B come to be disposed on a innermost semi-circle when they are represented by polar coordinates as shown in the lower chart in FIG. 3B while the SQUID magnetometers disposed on the eighth row between the positions of the reference numbers 23-*a* and 23-*d* shown in the middle chart in FIG. 3B come to be disposed on an outermost semi-circle when they are represented by polar coordinates as shown in the lower chart in FIG. 3B. More concretely, in the middle and lower charts in FIG. 3B, the position of the reference number 23-*b* corresponds to the position of the reference number 25-*b*, the position of the reference number 23-*c* corresponds to the position of the reference number 25-*c*, the position of the reference number 23-*a* corresponds to the position of the reference number 25-*a*, and the position of the reference number 23-*d* corresponds to the position of the reference number 25-*d* respectively.

The embodiment of the present invention can also apply to two-dimensional disposition of a plurality of SQUID magnetometers in any of a rectangular grid pattern, an oblique grid pattern, a concentric circle pattern, and a hexagonal pattern formed on a plane. Next, a description will be made for a case in which a plurality of SQUID magnetometers are disposed two-dimensionally in a K×M rectangular grid pattern consisting of K pieces (K: positive integer) in the x direction and M pieces (M: positive integer) in the y direction as shown in the upper chart in FIG. 3A. In the above description related to FIG. 3, in case the interval of the SQUID magnetometers in the x direction is assumed as dx and the interval of the SQUID magnetometers in the y direction is assumed as dy, the (expression 3) and the (expression 4) may be used instead of the (expression 1) and the (expression 2). In the (expression 3) and the (expression 4), k=1, 2, . . . , K and m=1, 2, . . . , M, and Δθ=180'/(M+1) are satisfied.

$$rk = k \times dx \quad \text{(Expression 3)}$$

$$\theta m = (M-m+1) \times \Delta\theta \quad \text{(Expression 4)}$$

Just like the case shown in FIG. 3, the SQUID magnetometers on the k-th row is positioned on a semi-circle having a radius rk=k×dx and disposed at a position having a deflection angle θm=(M−m+1)×Δθ (m=1, 2, . . . , M) at an equal angular interval Δθ from the base line. The SQUID magnetometers on the m-th column are disposed at a position having a radius vector rk=k×d (k=1, 2, . . . , K) at a deflection angle θm=(M−m+1)×Δθ.

The positions of the SQUID magnetometers at the front and back side measuring positions of the rectangular coordinates (x,y) are thus converted to the coordinates of the positions of the SQUID magnetometers of the front and back side measuring positions that use polar coordinates (r,θ) as described above just like the case shown in FIG. 3 in which a plurality of SQUID magnetometers are disposed two-dimensionally in a square grid pattern on a plane.

Furthermore, in the case of two-dimensional disposition of a plurality (L (L: positive integer)) of SQUID magnetometers in any of a rectangular grid pattern, an oblique grid pattern, a concentric circle pattern, and a hexagonal pattern formed on a plane, the following method is easy to realize the disposition. At first, the center of the region in which a plurality of SQUID magnetometers are disposed is assumed as a pole and a contour pattern connecting the positions of SQUID magnetometers on the radius vector furthest from the pole among the plurality of deflection angles is found. Then, a square that inscribes or circumscribes the contour pattern is found. After that, positions of the N×N (N: positive integer) SQUID magnetometers disposed at equal intervals are set virtually in the square. The magnetocardiogram waveform at each of the N×N points is found with an arithmetic processing through interpolating or extrapolating that uses the magnetocardiogram waveform at each of the N×N time-points measured actually with use of L SQUID magnetometers. In order to make the interpolation more accurately, L≧N×N should be satisfied. After obtaining the magnetocardiogram waveform at each of the N×N positions, the procedures described above with reference to FIG. 3 may be employed.

Furthermore, the present invention can apply even to two-dimensional disposition of a plurality (L (L: positive integer)) of SQUID magnetometers in any of a rectangular grid pattern, an oblique grid pattern, a concentric circle pattern, and a hexagonal pattern on an inner concave surface having a predetermined curvature. In that connection, the following method is effective to realize the disposition. At first, the positions of the L SQUID magnetometers disposed on an inner concave surface are projected on a plane vertical to the center axis of the concave surface or each SQUID magnetometer is positioned on a plane vertical to the center axis of the concave surface so as to be proportional to the distance between each of the L SQUID magnetometers and the center axis of the concave surface. After that, just like in the above case, the positions of the N×N (N: positive integer) SQUID magnetometers disposed at equal intervals are set inside a square virtually (including the periphery). The procedures described above may also be employed for the following processings. In case there is no center axis for the concave surface, a center axis may be found approximately and used.

As described above, the above embodiment of the present invention can apply to any two-dimensional disposition of a plurality of SQUID magnetometers.

Figure 4:
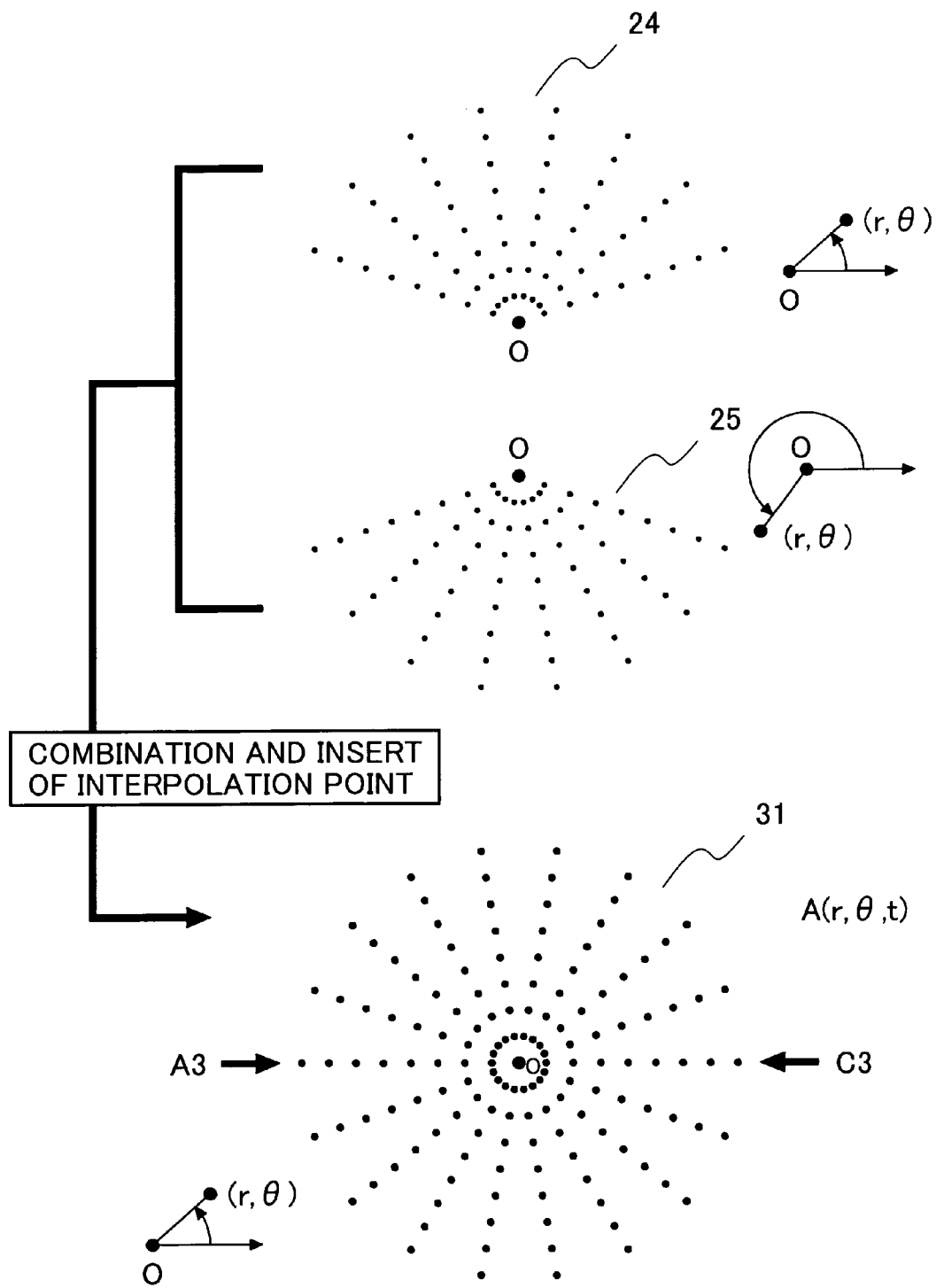
FIG. 4 illustrates how a magnetocardiogram waveform is measured from two directions on one planispheric chart in the embodiment of the present invention.

FIG. 4 shows a chart for describing a measuring position of a magnetocardiogram waveform from two directions with use of one planispheric chart (display with polar coordinates) in the above embodiment of the present invention.

As described with reference to FIG. 3, the coordinates of the position of each of the SQUID magnetometers at the front measuring position 24 and the back side measuring position 25 represented by polar coordinates (e,θ) are converted here.

As shown in the lower charts in both FIGS. 3A and 3B, as well as in the upper chart in FIG. 4, the measuring points of the object magnetocardiogram waveform, represented by polar coordinates (r,θ), are not displayed at the positions having deflection angles θ=0° and 180°. As shown schematically in FIG. 4, therefore, the polar coordinates (r,θ) related to the front side measuring position 24 and the polar coordinates (r,θ) related to the back side measuring position 25 are used to set virtual measuring positions at deflection angles θ=0° and 180° (hereinafter, to be also referred to as "virtual points" and these virtual points are assumed to be included in measuring positions and measuring points). And, as shown in FIG. 4, virtual N (N=8 here) measuring positions (virtual points) (disposed on each of radius vectors denoted with A3 and C3) are set at intervals d at each of deflection angle θ=0° and 180°.

And, as shown in the lower chart in FIG. 4, the SQUID magnetometers on the i-th row are positioned on a semi-circle having a radius ri=i×d as denoted by polar coordinates (r,θ) having both of a common polar O and a common base line. Those magnetometers are thus disposed at positions at a deflection angle θj=(N−j+1)×Δθ (j=0, 1, 2, . . . , N, N+1), . . . 2N, 2N+1) and at equal intervals Δθ from this base line while the SQUID magnetometers on the j-th column are disposed on a radius vector ri=i×d (j=0, 1, 2, . . . , N, N+1, . . . , 2N+1) and at a deflection angle θj (N−j+1)×Δθ. An object planispheric chart 31 is thus obtained. The chart 31 denotes the positions of 2N+2 SQUID magnetometers in total disposed at equal intervals in the directions of both deflection angle and radius vector.

At SQUID magnetometer positions at both of the front measuring position 24 and the back measuring position 25 except for those disposed on the radius vectors of A3 and C3 respectively as shown in FIG. 4, there is a magnetocardiogram waveform actually to be measured corresponding to each of the (2N+2) positions (including the virtual ones) of disposed SQUID magnetometers. The front side measuring position 24 and the back side measuring position 25 shown in the lower charts in FIGS. 3A and 3B, as well as the upper chart in FIG. 4 correspond to the front side measuring position 21 and the back side measuring position 22 shown in the upper charts in FIGS. 3A and 3B, respectively.

The magnetocardiogram at each of the N measuring points (virtual points) on each of the A3 and A3 radius vectors is found through interpolation with reference to FIG. 6 as to be described later.

As described above, measuring positions displayed with polar coordinates where each magnetocardiogram waveform is measured from two directions are combined, then measuring positions that are not displayed on the radius vectors are inserted to obtain one planispheric chart 31 for denoting a plurality of measuring positions disposed at equal intervals in each of the two directions of deflection angle and radius vector. This planispheric chart 31 is equivalent to a Bull's eye map.

Each point in the planispheric chart 31 is set to correspond to a magnetocardiogram and/or both of a scalar value and a vector value obtained from the magnetocardiogram at a point of time t. In other words, at each point of the planispheric chart 31 is displayed a scalar value and/or vector value at the point of time t in colors according to the size while the planispheric chart 31 is displayed on the display device together with the magnetocardiogram waveform at each measuring point. At that time, it is also possible to display only the planispheric chart 31 or display the scalar value and/or vector value without displaying the magnetocardiogram waveform.

In this example, the pole O of the planispheric chart 31 shown in the lower chart in FIG. 4 is positioned corresponding to the lower tip part (apex cordis) of the subject heart. The measuring points of the magnetocardiogram waveform are displayed on the display device so that the inspection engineer and/or doctor can observe the scalar value and/or vector value obtained from each magnetocardiogram waveform measured at each of those measuring points.

Each CAM displayed on one planispheric chart 31 at the point of time t can be represented by a distance r from the lower tip (apex cordis) of the subject heart, a deflection angle θ, a function assumed at the point of time t, and A (r, θ, t).

As described above, in the embodiment of the present invention, each of the points including virtual ones displayed on one planispheric chart 31 with polar coordinates as shown in the lower chart in FIG. 4 is regarded as a measuring point. Both waveform and value obtained from a magnetocardiogram measured at each of those points are set to correspond to the point to obtain a planispheric chart 31 that represents various kinds of waveforms, various kinds of maps, etc., which can be displayed. In other words, a magnetocardiogram is measured from two directions, that is, from both of the thoracic (front) side and the back side, then the measured magnetocardiogram or a map obtained from the magnetocardiogram measured from the two directions and denoting the subject's heart state (for example, presence of any disease) can be displayed on one planispheric chart 31 with polar coordinates.

For example, it is possible to display each value or average value of various kinds of waveforms of a magnetocardiogram measured repetitively, as well as each value or average value of such waveforms as P, QRS, T, etc. extracted from a magnetocardiogram measured repetitively.

Various types of maps are also displayed on each magnetocardiogram. Those maps are, for example, an equal magnetic-field-line chart connecting equal points at a specified point of time (for example, a point at which each of such waveforms as P, Q, R, S, T, etc. reaches its maximum) of magnetocardiogram waveforms measured at each point or in a time phase (for example, a time band in which such a waveform as P, QRS, T, or the like appears), equal integral chart connecting equal points of integrated values of each value or average value of magnetocardiogram waveforms in a predetermined time band (for example, a time band in which such a waveform as P, QRS, T, or the like appears), a current distribution chart (CAM, etc.), an absolute value map in a CAM, a phase value map in a CAM, etc.

And, in case a CRM (current ratio map) obtained from magnetic cardiogram waveforms measured from two directions, that is, from the thoracic (front) side and from the back side is displayed on a planispheric chart 31 with polar coordinates before and after exercise stress, it is easy to observe the state of the heart disease of each patient.

Hereinafter, as a typical example for using a planispheric chart 31 to display the status of such a heart disease, a current distribution chart (CAM) will be described. In the following embodiment of the present invention, a component (Bz) of a magnetocardiogram in the normal line is measured.

The CAM uses a pseudo current vector I (x direction component: Ix=dBz/dy, y direction component: Iy=−dBz/dx) found by differentiating a magnetic field (Bz) to be measured. It is also possible to find a lead field inverse matrix as a current distribution to obtain such a current vector. The present invention is not limited only to the use of such pseudo current vectors.

Instead of measuring the normal line direction component (Bz) of a magnetocardiogram, it is also possible to measure the tangential component (Bx, By) of the magnetocardiogram to find a CAM with use of a well-known method. Consequently, the embodiment of the present invention can apply to measuring of such tangent components (Bx, By) of the magnetocardiogram.

As to be described in detail later, each CAM displayed on one planispheric chart 31 can be represented by a distance r from the tip part (apex cordis) of a subject heart, a function of a deflection angle θ, and A (r,θ,t).

Figure 5:
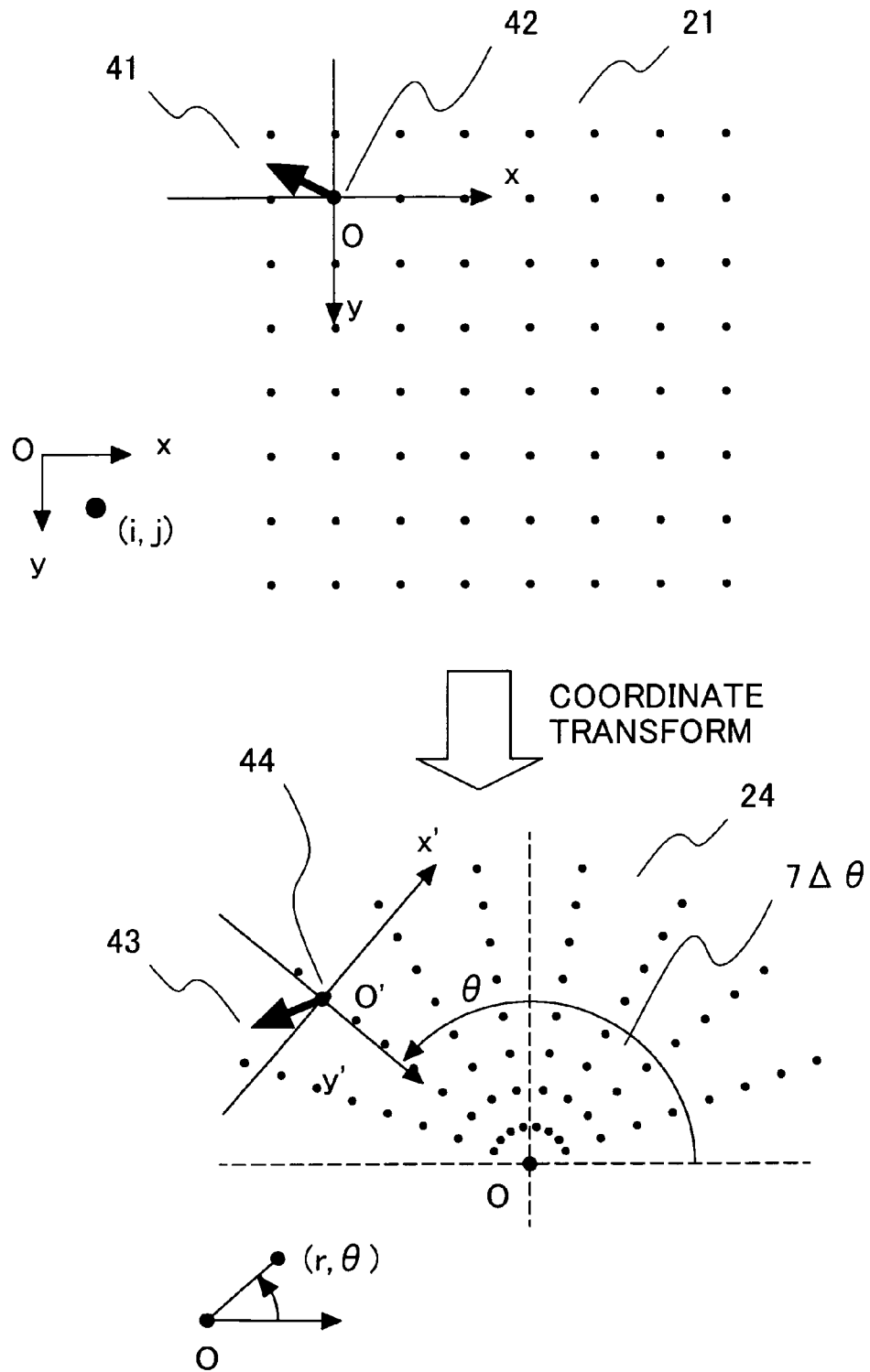
FIG. 5 illustrates how coordinates are converted in the I vector direction of a pseudo current vector in the embodiment of the present invention.

FIG. 5 shows a chart for describing how to convert coordinates in the vector direction of the pseudo current vector I. In FIG. 5, a current vector at each measuring point at the front side measuring position 21 will be described as an example.

A current vector I at a measuring point on the i-th row shown in the upper chart in FIG. 5 (upper chart in FIG. 3A) is positioned on a semi-circle having a radius ri=i×d and disposed at a position having a deflection angle θj=(N−j+1)×Δθ (j=1, 2, . . . , N) at equal angular intervals Δθ from the base line while the current vector I at a measuring point of the j-th row is disposed at a position having a radius vector ri=i×d (j=1, 2, . . . , N) at a deflection angle θj=(N−j+1)×Δθ. At that time, the forward direction of the x axis denoted with a broken line in the lower chart in FIG. 5 is assumed as the base line (the forward of the x axis in each of the upper charts in FIG. 5 and FIG. 3A is assumed as the base line) and the current vector I is rotated just by θj=(N−j+1)×Δθ−90°.

More concretely, for example, in the upper chart in FIG. 5, the coordinates of the current vector (before its rotation) 41 obtained at a measuring point on the 7th row and on the second column at the front side measuring position 21 shown in the upper chart in FIG. 3A is converted to those of the current vector (after its rotation) 43 shown at the front side measuring position 24 shown in the lower chart in FIG. 5 (lower chart in FIG. 3A and upper chart in FIG. 4). The forward direction of the x axis denoted with a broken line in the lower chart in FIG. 5 is assumed as the base line (the forward of the x axis in each of the upper charts in FIG. 5 and FIG. 3A) and the current vector I is rotated just by 7×Δθ−90° from the base line.

In other words, as shown in the upper chart in FIG. 5, the current vector (current arrow) 41 that assumes the origin O 42 (position of a measuring point on the 7th row and on the second column) of the local rectangular coordinates (x,y) obtained by moving the origin O of the rectangular coordinates (x,y) shown in the upper chart in FIG. 3A to the measuring point 42, the origin O 42, and the local rectangular coordinates (x,y) are rotated by an angle 7×Δθ around the origin O of the rectangular coordinates (x,y) that assumes the x axis as the base line to be moved to the current vector (current arrow) 43, the origin O' 44, and the local rectangular coordinates (x', y') respectively. The similar processing is done at each measuring point at the front side measuring position 21.

Completely the same processing as that for each measuring point of the front side measuring position 21 described above is effective for each measuring point of the back side measuring position 22 shown in the upper chart in FIG. 3B (that is, the back side measuring position 23) shown in the middle chart in FIG. 3B). Consequently, the description of the same processing will be omitted here to avoid redundancy.

While the rotation of a current vector that denotes a vector value is described above with reference to FIG. 5, the same description may also apply to the rotation of other vector values. When creating a distribution chart of scalar values that denote only sizes, there is no need to make the rotation processing as described with reference to FIG. 5.

Figure 6:
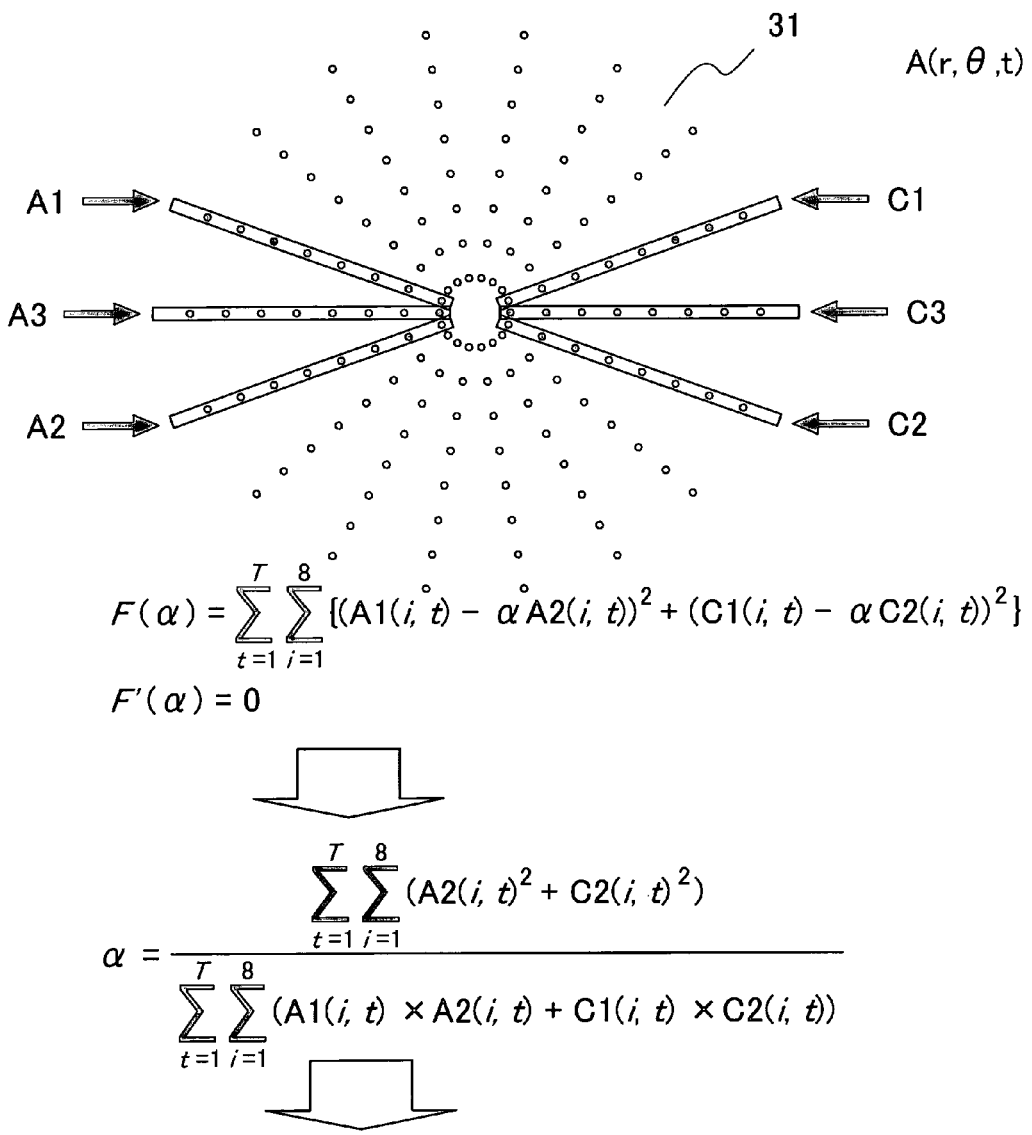
FIG. 6 illustrates how to obtain a magnetocardiogram through interpolation at each virtual measuring point on each of radius vectors A3 and C3 on the planispheric chart shown in FIG. 4.

FIG. 6 is a chart for describing a method for finding a magnetocardiogram at N measuring points (virtual points) on each of the radius vectors of A3 and C3 on the planispheric chart 31 shown in FIG. 4 by means of interpolation. This interpolation includes scale adjustment of each magnetocardiogram waveform measured from two directions.

In the upper chart in FIG. 6, the pole O of the planispheric chart 31, positioned in the center of the measuring point having the minimum radius vector r is omitted. Similarly, in the lower chart in FIG. 9, as well as in FIGS. 10A, 11A, 12A, 13A, 18, 19, and 22 to be described later, the pole O of the planispheric chart 31, positioned in the center of the measuring point having the minimum radius vector r is omitted.

The magnetocardiogram waveform at each of the N (N=8 here) measuring points (virtual points) on the A3 radius vector can be obtained through interpolation with use of each of the N measurement points on a radius vector A1 shown in FIG. 6 (radius vector closest to the deflection angle θ=180° at the front side measuring position 24 shown in each of the lower chart in FIG. 3A, the upper chart in FIG. 4, and the lower chart in FIG. 5), and on the radius vector A2 shown in FIG. 6 (the radius vector closest to the deflection angle θ=180° of the back side measuring position 25 shown in each of the lower chart in FIG. 3B and the upper chart in FIG. 4).

Similarly, the magnetocardiogram at each of the N measuring points (N=8 in this example) on the C3 radius vector can be obtained through interpolation with use of each of the N measurement points on the radius vector C1 shown in FIG. 6 (radius vector closest to the deflection angle θ=0° at the front side measuring position 24 shown in each of the lower chart in FIG. 3A and the upper chart in FIG. 4 and the radius vector C2 shown in FIG. 6 (the radius vector closest to the deflection angle θ=0° at the back side measuring position 25 shown in each of the lower chart in FIG. 3B and the upper chart in FIG. 4).

However, the magnetocardiogram data at measuring points on each of the A1, A2, C1, and C2 radius vectors, as well as every data between measurement times T are used to determine a weight coefficient α to be described later. A measurement time T usually means all the time bands of the P, QRS, and T waveforms in one heartbeat. However, the user can set the measurement time T in a predetermined fixed time band. The evaluation function F(α) used to determine such a weight coefficient α can be defined as shown in the (expression 5), for example. The F(α) shown in the (expression 5) is determined so as to satisfy the (expression 6) in which partial differential related to the weight coefficient α is set at zero. The weight coefficient α thus comes to be calculated with the (expression 7).

The magnetocardiogram waveform at each point of time t at each of the N measuring points on the A3 and C3 radius vectors can be calculated with the (expression 8) and (expression 9) with use of the weight coefficient α calculated in the (expression 7). The addition symbol Σ1 is executed for t=1, ..., T while the addition symbol Σ2 is executed for i=1, ..., N (N=8 in this example).

$$F(\alpha) = \Sigma 1 \Sigma 2 \{(A1(i,t) - \alpha A2(i,t))2 + (C1(i,t) - \alpha C2(i,t))2)\} \quad \text{(expression 5)}$$

$$F'(\alpha) = 0 \quad \text{(expression 6)}$$

$$\alpha = \Sigma 1 \Sigma 2 \{(A2(i,t)2 + C2(i,t))2\}/\{\Sigma 1 \Sigma 2 ((A1(i,t) \times A2(i,t) + C1(i,t) \times C2(i,t)))\} \quad \text{(expression 7)}$$

$$A3(i,t) = \{A1(i,t) + \alpha A2(i,t)\}/2 \quad \text{(expression 8)}$$

$$C3(i,t) = \{C1(i,t) + \alpha C2(i,t)\}/2 \quad \text{(expression 9)}$$

The signal intensity of the magnetocardiogram waveform at each measuring point at the back side measuring position 25 on the planispheric chart 31 is adjusted in scale of the α (weight coefficient) times to match with the signal intensity of the magnetocardiogram waveform measured at each measuring point at the front side measuring position 24.

There is a large difference between the intensity of the magnetocardiogram waveforms measured from the front side measuring position 21 and that measured from the back side measuring position 22. This is why the magnetic field intensity comes to be discontinued, thereby unnatural map distortion occurs when observing a display of an obtained result in case magnetocardiogram waveforms measured from two directions are just combined. To void this discontinuity, scale adjustment should preferably be done with use of an α (weight coefficient).

When displaying an output of the planispheric chart 31, the signal intensity of a magnetocardiogram waveform at each measuring point at the front side measuring position 24 is displayed on the display device together with the signal intensity of the magnetocardiogram waveform measured at each scale-adjusted measuring point at the back side measuring position 25.

As an alternative method, it is also possible to multiple the signal intensity of the magnetocardiogram at each measuring point of the front side measuring position 24 by (1/α) (α=weight coefficient) to make such scale adjustment for the signal intensity of the magnetocardiogram waveform measured at each measuring point on the back side measuring position 25. The signal intensity of the magnetocardiogram at each measuring point at the back side measuring position 25 may be displayed on the display device together with the signal intensity of the magnetocardiogram waveform measured at each scale-adjusted measuring point at the front side measuring position 24.

The above interpolation makes it possible to display the magnetocardiogram at every measuring point on the planispheric chart 31 continuously and smoothly. In the description shown in FIG. 6, interpolation is done for N points (N=8) on each of the A3 and C3 radius vectors. In a variation, however, there is no need to fix the number of measuring points at N; the number of measuring points may be more than N or less than N, of course. In another variation, no interpolation is required for any measuring points on the A3 and C3 radius vectors and values on the radius vector A1 or A2 may be disposed on the radius vector A3 and the values on the radius vector C1 or C2 may be disposed on the radius vector C3.

The evaluation function used to determine a weight coefficient α is not limited only to that in the (expression 5); various kinds of functions that can display the values of all the measuring point on the subject planispheric chart 31 smoothly and continuously can be selected as examples, of course.

In still another variation, no data is set to correspond to the radius vectors A3 and C3 and no interpolation is done for any of the radius vectors A3 and C3, that is, no data is set to correspond to each measuring point at both of the front side measuring position 24 and the back side measuring point 25 and the data related to each measuring point of the front side measuring position 24 is set to correspond to a region having a deflection angle 0°<θ<180° of one planispheric chart 31 without connecting the data related to each measuring point of the front side measuring position 24 (magnetocardiogram data and/or a scalar value and/or vector value obtained from the magnetocardiogram data) to the data related to each measuring point of the back side measuring position 25 (magnetocardiogram data and/or scalar value and/or vector value obtained from the magnetocardiogram data) through a line, then the data related to each measuring point of the back side measuring position 25 is set to correspond to a region having a deflection angle θ of 180°<θ<360° of one planispheric chart 31.

At that time, the data related to each measuring point of the back side measuring position 25 is multiplied by a (weight coefficient) or data related to each measuring point of the front side measuring position 24 is multiplied by (1/α) (α=weight coefficient). In this variation, some data is lost between the front side measuring position 24 and the back side measuring position 25, but the data related to each measuring point of the front side measuring position 24 and the back side measuring position 25 can be displayed almost smoothly and continuously.

It is also possible to find both scalar and vector values from each magnetocardiogram waveform at the front side measuring position 24 and at the back side measuring position 25 and magnetocardiogram waveform and/or scalar and vector values obtained from those waveforms are set to correspond to each measuring point on the planispheric chart 31 as described above. In case such scalar and vector values are not found on any radius vector from which any of a scalar value and a vector value obtained from magnetocardiogram waveforms are lost can be obtained through interpolation or with use of a variation example just like the insertion of a magnetocardiogram waveform, of course.

It is also possible to obtain scalar and vector values from the magnetocardiogram waveform measured at each measuring point of the front side measuring position 21 and the back side measuring position 22 and those obtained scalar and vector values may be converted in the processing procedures shown in FIGS. 3 through 6, of course.

Figure 7:
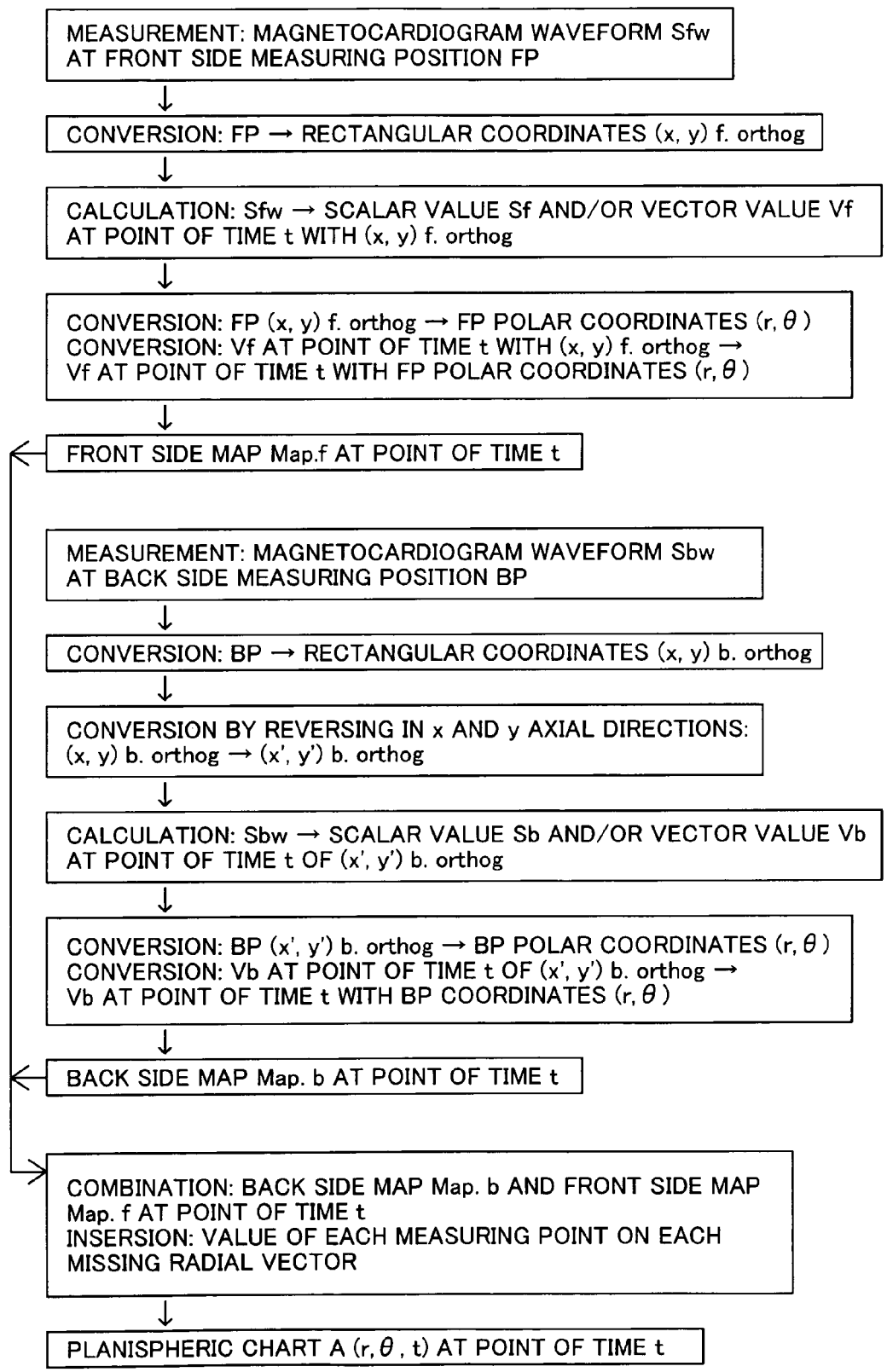
FIG. 7 is a flowchart of creating a planispheric chart in the embodiment of the present invention.

FIG. 7 is a flowchart of processings of how to create a planispheric chart A (r,θ,t) in the above embodiment of the present invention.

At first, (1) the magnetocardiogram waveforms Sfw and Sbw are measured at the front and back side measuring positions FP and BP respectively.

(2) Coordinates of the front side measuring position FP are converted to the rectangular coordinates (x,y) f.orthog and coordinates of the back side measuring position BP are converted to the rectangular coordinates (x,y) b.orthog respectively to find each position disposed in an N×N square grid pattern.

Next, this conversion will be described with respect to a case in which SQUID magnetometers are not disposed in a square grid pattern on a plane. For example, in case SQUID magnetometers are disposed two-dimensionally in any of a rectangular grid pattern, an oblique grid pattern, a concentric circle pattern, and a hexagonal pattern formed on a plane, the following procedures (a1), (b1), and (c1) can be employed.

(a1) As described above, at first, the center of a region in which a plurality of SQUID magnetometers are displayed is determined as a pole, then searching is made for a contour chart that connects a SQUID magnetometer positioned on the farthest radius vector from the pole among the positions of a plurality of deflection angles.

(b1) A square inscribed or circumscribed in the contour chart is found. Then, positions of the N×N (N: positive integer) SQUID magnetometers disposed at equal intervals are set virtually in this square (including those at the outer periphery).

(c1) The magnetocardiogram waveform at each point of time at each of the N×N positions is found through an arithmetic processing by interpolation or extrapolation with use of the magnetocardiogram waveform to be measured at each point of time actually with use of L SQUID magnetometers.

In the case of two-dimensional disposition in any of a rectangular grid pattern, an oblique grid pattern, a concentric circle pattern, and a hexagonal pattern on a convex inner surface having a predetermined curvature, the following procedures (2) and (b2) can be employed.

(a2) As described above, at first, the positions of the SQUID magnetometers disposed on a concave inner surface are projected on a plane vertical to the center axis of the concave surface or position of each SQUID magnetometer is set on the plane vertical to the center axis of the concave surface in proportion to a distance between each of the SQUID magnetometer positions and the center axis of the concave surface.

(b2) After that, similarly to the above examples (a1) and (b1), the positions of the N×N (N: positive integer) SQUID magnetometers disposed at equal intervals are set virtually in a square (including those at the outer periphery), then the processing (c1) is executed again.

(3) The coordinates of the back side measuring position BP are inverted in the x and y directions of the rectangular coordinates (x,y) b.orthog to find the coordinates of the back side measuring position BP of the rectangular coordinates (x', y') b.orthog.

(4) The scalar value Sf and/or vector value Vf at the rectangular coordinates (x,y) f.ptyjog at a point of time t is found from the magnetocardiogram waveform Sfw at the front side measuring position FP and the scalar value Sb and/or vector value Vb at the rectangular coordinates (x', y') b.ptyjog at a point of time is found from the magnetocardiogram waveform Sfw at the front side measuring position BP respectively.

(5) The front side measuring position FP at the rectangular coordinates (x,y) f.orthog, as well as the vector value Vf at a point of time t are converted to polar coordinates (r,θ) of the front side measuring position FP respectively and a planispheric chart corresponding to the front side measuring position FP, that is, a front side map Map.f at a point of time t is found. Then, the scalar value Sb and/or vector value Vb at the rectangular coordinates (x', y') b.orthog at a point of time t are converted to the polar coordinates (r, θ) of the back side measuring position BP respectively to find a planispheric chart corresponding to the back side measuring position BP, that is, a back side map Map.b at a point of time t.

(6) The back side map Map.b and the front side map Map.f at a point of time t are combined to insert a value of each measuring point on each radius vector from which measuring point values are lost through an arithmetic processing by interpolation to obtain one planispheric chart A (r,θ,t) that provides maps in which the values of all the measuring points on the planispheric chart are displayed continuously and smoothly.

As described above, in (1), it is possible to obtain scalar values Sf and Sb, as well as vector values Vf and Vp at a point of time from the magnetocardiogram waveforms Sfw and Sbw measured at measuring points of both of the front measuring position FP and the back side measuring position BP respectively. It is also possible to convert the scalar values Sf and Sb at a point of time t and the vector values Vf and Vb at a point of time at each measuring point of both of the front side measuring position FP and the back side measuring position BP in the processing procedures shown in FIGS. 3 through 6. In that connection, calculation of the scalar value Sb and/or vector value Vb at a point of time in (4), as well as conversion of the scalar value Sb and/or vector value Vb at a point of time in (5) can be omitted.

Hereinafter, a description will be made for the effects to be obtained concretely in the above embodiment of the present invention with use of the data measured actually with respect to a healthy person shown in FIGS. 8 through 12.

Figure 8A:
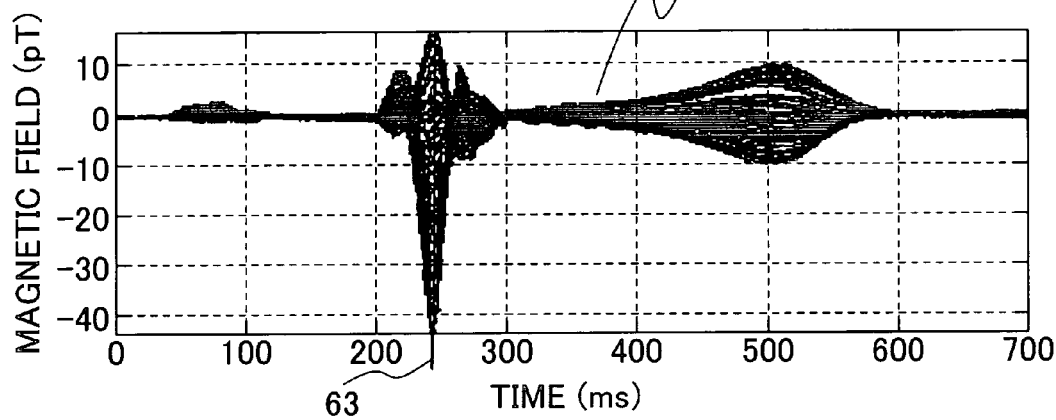
FIG. 8 is graphs for showing a magnetocardiogram of a healthy person in the embodiment of the present invention.
Figure 8B:
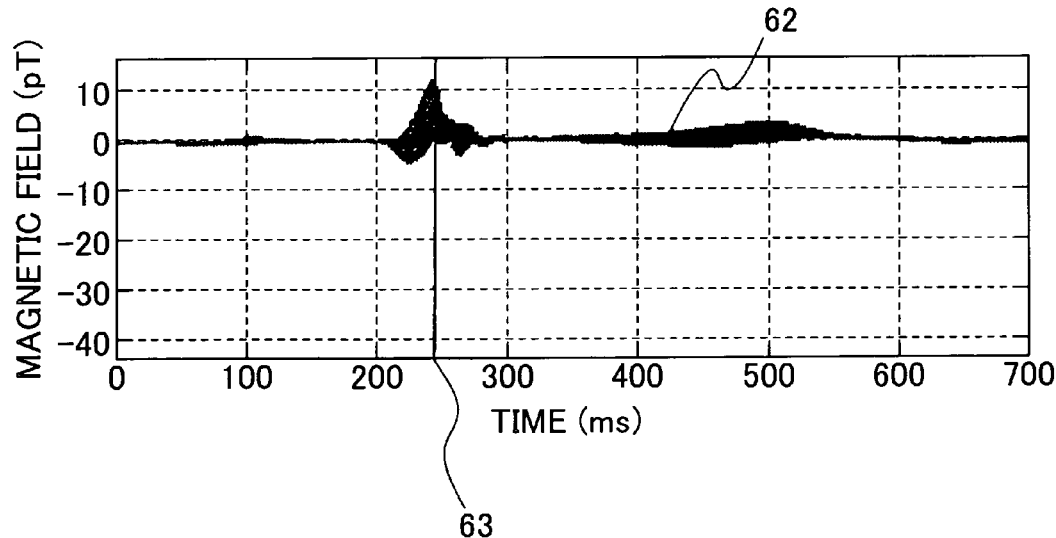

FIG. 8 shows a graph for describing magnetocardiogram waveforms related to the healthy person measured in the above embodiment of the present invention. The magnetocardiogram waveform shown in FIG. 8 is that of a healthy person measured with 64 channels of magnetic sensors disposed in an 8×8 square grid pattern composed as shown in FIGS. 1 and 2 on a plane. FIG. 8B and FIG. 8B show graphs in which magnetocardiogram waveforms 61 and 62 measured with magnetic sensors of 64 channels disposed at both front (thoracic) and back side measuring positions are superposed.

The horizontal axis of the magnetocardiogram waveform 61 measured at the front side measuring position in FIG. 8A and the horizontal axis of the magnetocardiogram waveform 62 measured at the back side measuring position in FIG. 8B denote a point of time (ms) at which magnetocardiogram waveforms from both front and back side measuring positions are aligned in point of time with reference to the point of time of the R-wave peak of the second inductive electrocardiogram measured simultaneously at the same electrode position when in measuring. The vertical axes in FIG. 8A and FIG. 8B denote the intensity (pT) of a magnetocardiogram waveform respectively.

A time of point line 63 vertical to the horizontal axis in FIG. 8A and FIG. 8B denotes a point of time for displaying mapping data of such a contour chart as a current distribution chart (CAM or the like), an equal magnetic field chart, an equal integral chart, or the like with use of the planispheric chart 31 shown in the lower chart in FIG. 4 and FIG. 6. FIG. 8A and FIG. 8B can display a plurality of point of time lines 63 while only one point of time line 63 at a peak of the R wave is displayed here. FIG. 8A and FIG. 8B can also display map data at a plurality of points of displaying time.

FIGS. 9 through 12 show actual examples of displaying a CAM obtained from each magnetocardiogram waveform measured actually on one planispheric chart.

Figure 9:
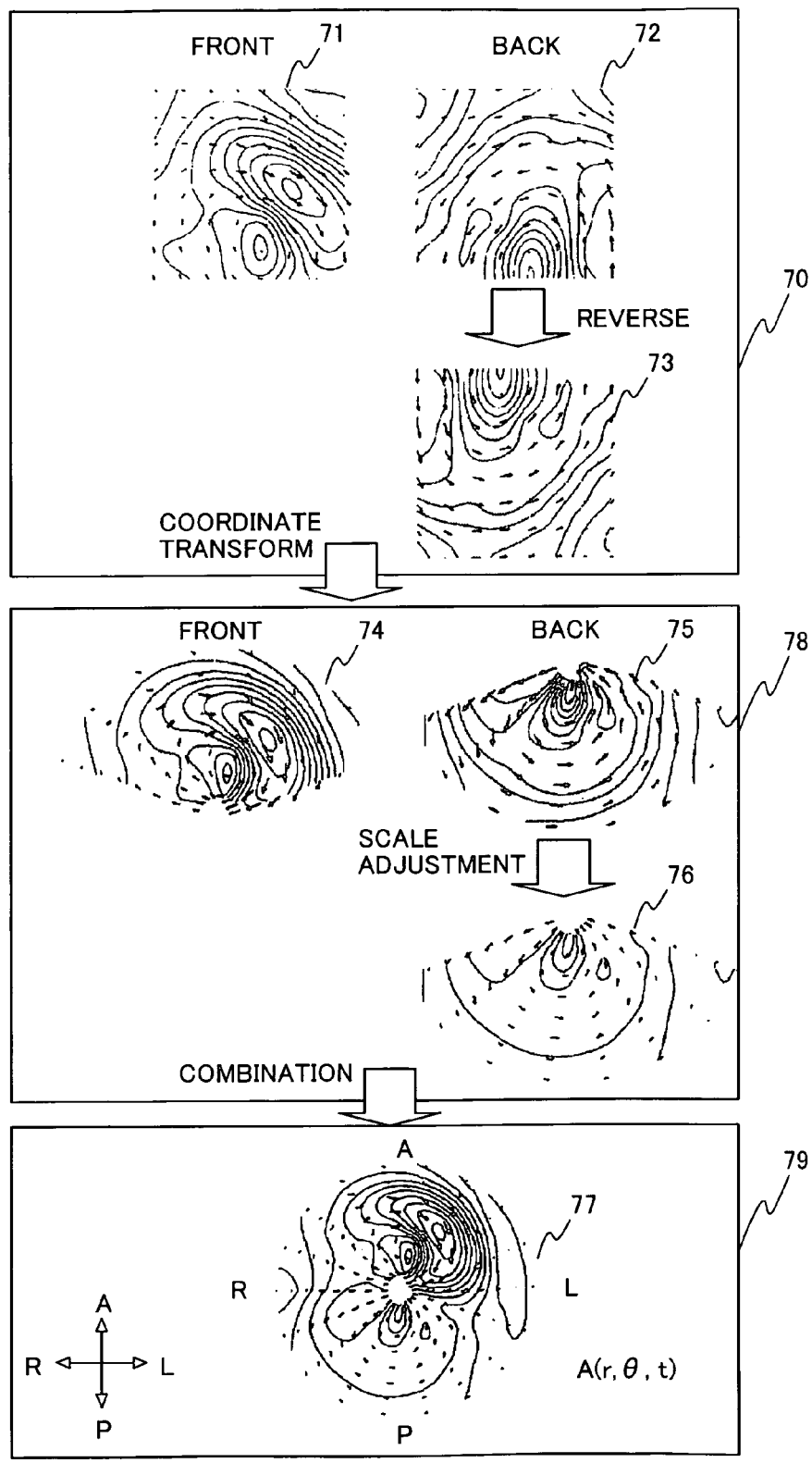
FIG. 9 how the processing in each of FIGS. 3 through 7 obtains a result with use of measured data on a point of time line 63 shown in FIGS. 8A and 8B.

FIG. 9 shows a chart for denoting an outline and a concrete example of a result of processings including coordinate conversion described with reference to FIGS. 3 through 7 with use of measured data at a point of time 63 of the peak of the R wave of the magnetic cardiogram related to the healthy person shown in FIGS. 8A/B.

(First processing 70): A CAM 71 is calculated from a magnetocardiogram waveform measured at the front side measuring position 21 and a CAM 72 is calculated from a magnetocardiogram waveform measured at the back side measuring position 22, then the displayed coordinates of the CAM 72 are inverted in both x and y directions to obtain a CAM 73.

(Second processing 78): The rectangular coordinates of both CAM 71 and CAM 73 are converted to polar coordinates respectively to obtain a CAM 74 at the front side measuring position 21 and a CAM 75 at the back side measuring position 22 displayed at polar coordinates respectively. The CAM 75 is adjusted to the CAM 74 in scale with use of a weight coefficient α to obtain a CAM 76.

(Third processing 79): The CAM 74 obtained from the magnetocardiogram waveform measured at the front side measuring position 21 is combined with the CAM 76 obtained from the magnetocardiogram waveform measured at the back side measuring position 22. The CAM data at the measuring points on each missing radius vector is inserted through an arithmetic processing by interpolation to obtain a planispheric chart (at a point of time t) A (r,θ,t) that provides a map in which the CAM data values at all the measuring points on the planispheric chart 77 are displayed smoothly and consecutively.

In the CAM 71 to 76 shown in FIG. 9 (processing 70) to (processing 79), the planispheric chart 77, as well as FIG. 10A, FIG. 11A, FIG. 12A, and FIG. 13 to be described later, each arrow denotes a current vector, each arrow length denotes the absolute value (size) of the current vector, each arrow direction denotes a direction of the current vector, and each curve denotes a contour map in which points of equal absolute values of current vectors are connected.

In the arrow map that denotes distribution of current vectors to be used in the following description, a contour map is displayed together with each current vector denoted with an arrow at each measuring point. Also in the CAMs 71 to 76, as well as in the planispheric chart 77, each measuring point denoted with a small dot and the middle point in each arrow are set to match with each other in the display.

In the display of the planispheric chart 77 shown in the lower chart in FIG. 9, the symbols L, R, A, and P are capital letters of "Left", "Right", "Anterior", and "Posterior" that denote directions. In the following description, they will be abbreviated as L part, R part, A part, and P part respectively to make it easier to understand a place in which electrical excitation is to be recognized. In FIGS. 10 through 13, 18, and 19, symbols L, R, A, and P are also displayed similarly. Intersecting points of a line for connecting the L, R, A, and P match with the pole O (not shown) respectively in the planispheric chart 31.

Figure 10A:
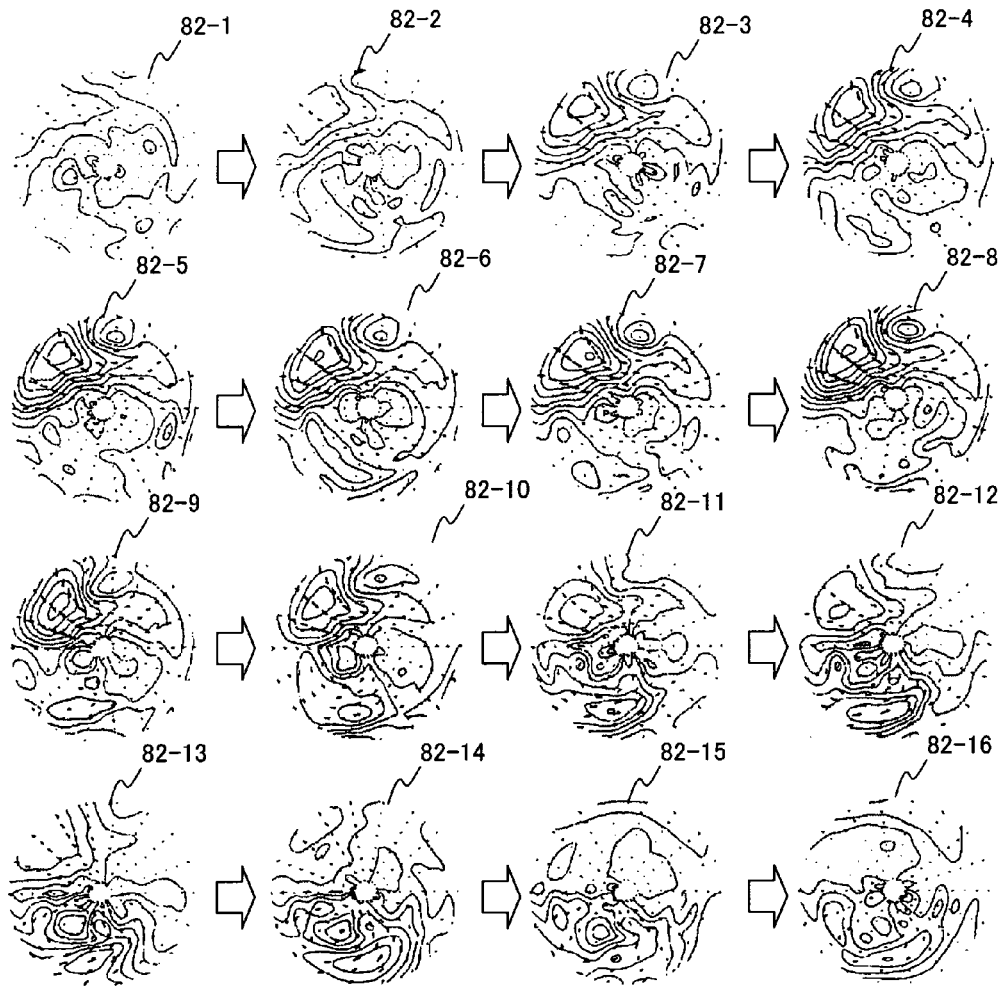
FIG. 10 illustrates how a CAM obtained in the embodiment of the present invention changes with time in a P-wave time band.
Figure 10B:
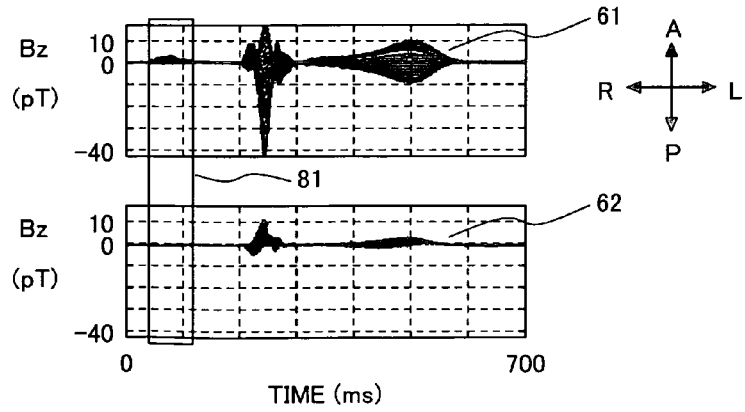

FIG. 10 shows a chart for describing changes of a CAM with time in a time band of the P wave, obtained in the embodiment of the present invention. FIG. 10A shows changes of the CAM with time in the time band of the P wave at time intervals obtained by dividing the time band of the P wave equally into 16 sections in each of the magnetocardiogram waveforms 61 and 62 shown in FIGS. 8A and 8B sequentially in an ascending order of the points of time in the planispheric charts 82-1 to 82-16. FIG. 10B shows the time band of the P wave in magnetocardiogram waves 61 and 62 shown in FIGS. 8A and 8B.

In FIG. 10A, each measuring point in each of the 82-1 to 82-16 planispheric charts denotes an A (r,θ,t) at a point of time t, a distance r, and a deflection angle θ in a time band of the P wave. Aksi in each of FIGS. 11A, 12A, and 13 to be described later, the A (r,θ,t) is shown similarly.

In each time band between the planispheric charts 82-2 to 82-11, electrical excitation is recognized mainly in the R part (around the right atrium) at the A part side. In each time band between the planispheric charts 82-10 and 82-16, such electrical excitation is also recognized around the center part (around the left atrium) at the P part side. This is why it is easy to understand at a glance of the object CAM displayed on one planispheric chart that current distribution is caused by the electrical excitation in both of the right and left atriums in different time bands.

Figure 11A:
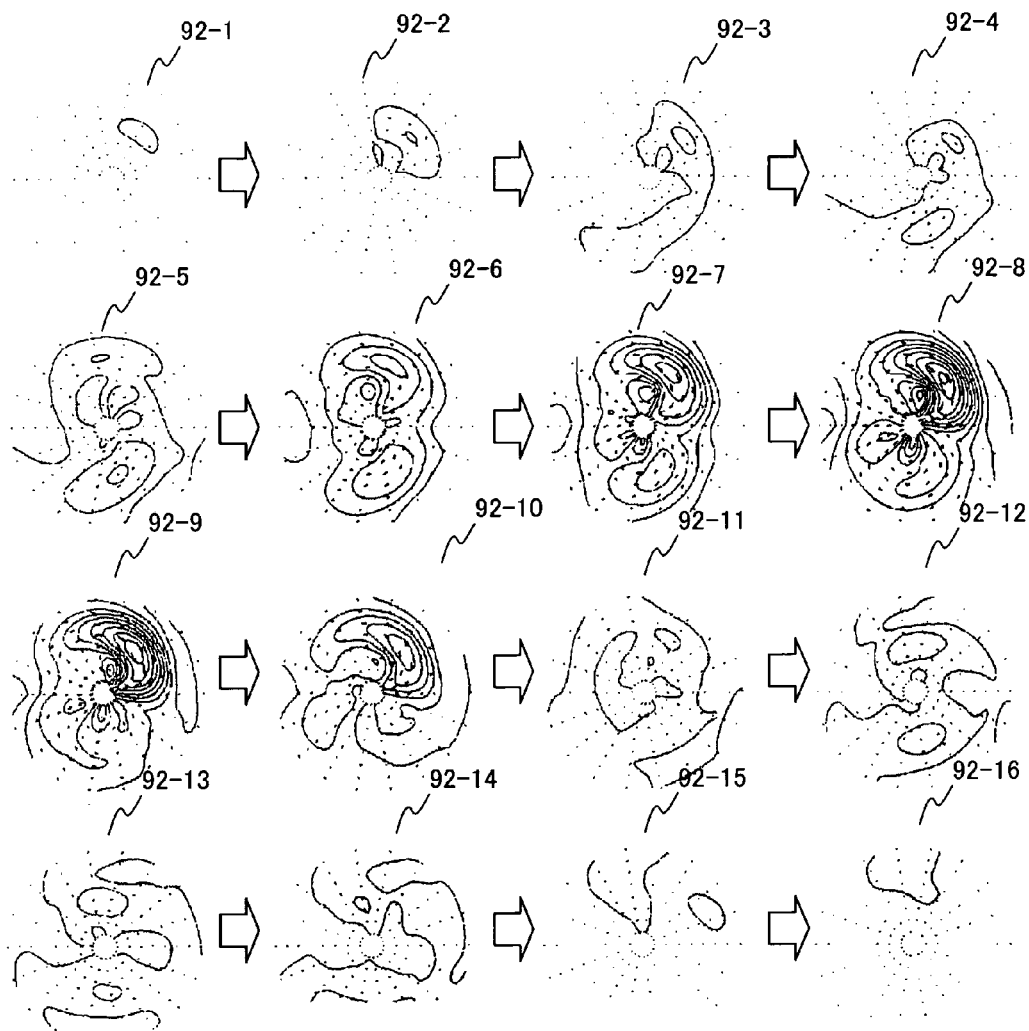
FIG. 11 illustrates how a CAM obtained in the embodiment of the present invention changes with time in a QRS composite wave time band.
Figure 11B:
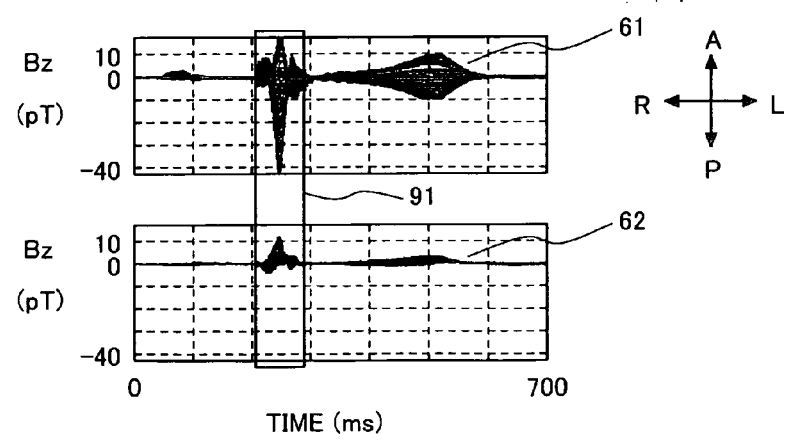

FIG. 11 shows a chart for describing changes of a CAM with time in a time band of the QRS complex waveform obtained in the embodiment of the present invention. FIG. 11A shows changes of the CAM with time in a QRS complex waveform time band obtained by dividing the time band of the QRS complex waveform in the magnetocardiogram waveforms 61 and 62 shown in FIGS. 8A and 8B sequentially into 18 sections and arranged in an ascending order of the points of time in the planispheric charts 92-1 to 92-16 (A(r,θ,t)). FIG. 11B shows a time band 91 of the QRS complex waveform in the magnetocardiogram waveforms 61 and 62 shown in FIGS. 8A and 8B.

In each time band between the planispheric charts 92-6 to 92-10, electrical excitation is recognized mainly in the L part (around the left atrium) at the A part side. At the same point of time, such electrical excitation is also recognized around the L part at the P part side (at the posterior of the left atrium), although the excitation is weak. Such way, it is understand that electrical excitement occurs at the same point of time in the whole left atrium (both anterior and posterior sides) and even normal depolarization occurrence in the left atrium of the subject heart can be checked at a glance.

Figure 12A:
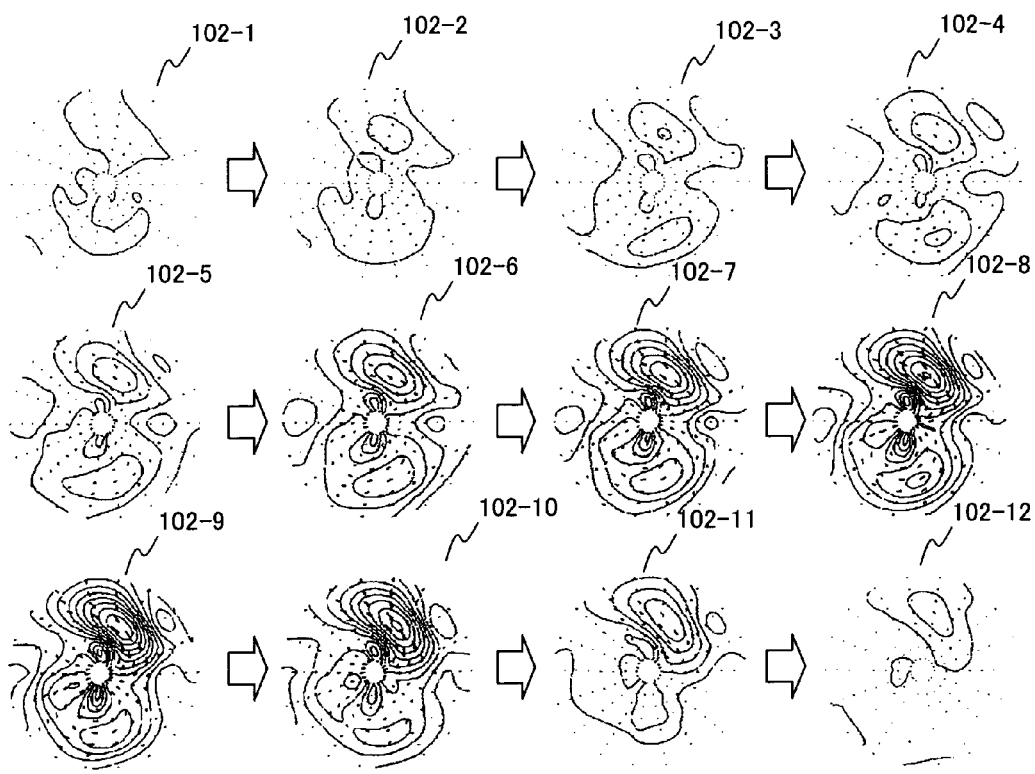
FIG. 12 illustrates how a CAM obtained in the embodiment of the present invention changes with time in a T wave time band.
Figure 12B:
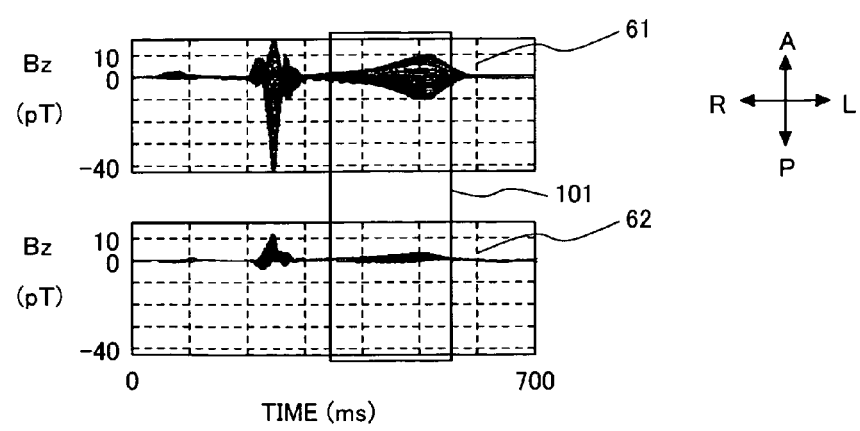

FIG. 12 shows a chart for describing changes of a CAM with time in a time band of the T waveform obtained in the embodiment of the present invention. FIG. 12A shows changes of the CAM with time in a T waveform time band obtained by dividing the time band of the T waveform in the magnetocardiogram waveforms 61 and 62 shown in FIGS. 12A and 12B sequentially into 12 sections and arranged in an ascending order of the points of time of the planispheric charts 102-1 to 102-12 (A(r,θ,t)). FIG. 12B shows a time band 101 of the T waveform in the magnetocardiogram waveforms 61 and 62 shown in FIGS. 8A and 8B.

Changes of the CAM with time between planispheric charts 102-1 102-12 shown in FIG. 12A denotes occurrence of electrical excitement mainly in the L part (around the left atrium) at the A part side. At the same point of time, such electrical excitation is also recognized around the L part at the P part side (at the posterior of the left atrium), although the excitation is weak. Such way, it is understand that electrical excitement occurs at the same point of time in the whole left atrium (both anterior and posterior sides) and even normal depolarization occurrence in the left atrium of the subject heart can be checked at a glance.

In a re-polarizing time band (a time band in which a T wave is generated from an ST wave), a patient of ischemic cardiac disease is apt to generate a deviation in current direction, re-polarizing time, etc. and this is why the embodiment of the present invention makes it easier to find an abnormality just by looking at each displayed CAM with use of one planispheric chart.

Figure 13:
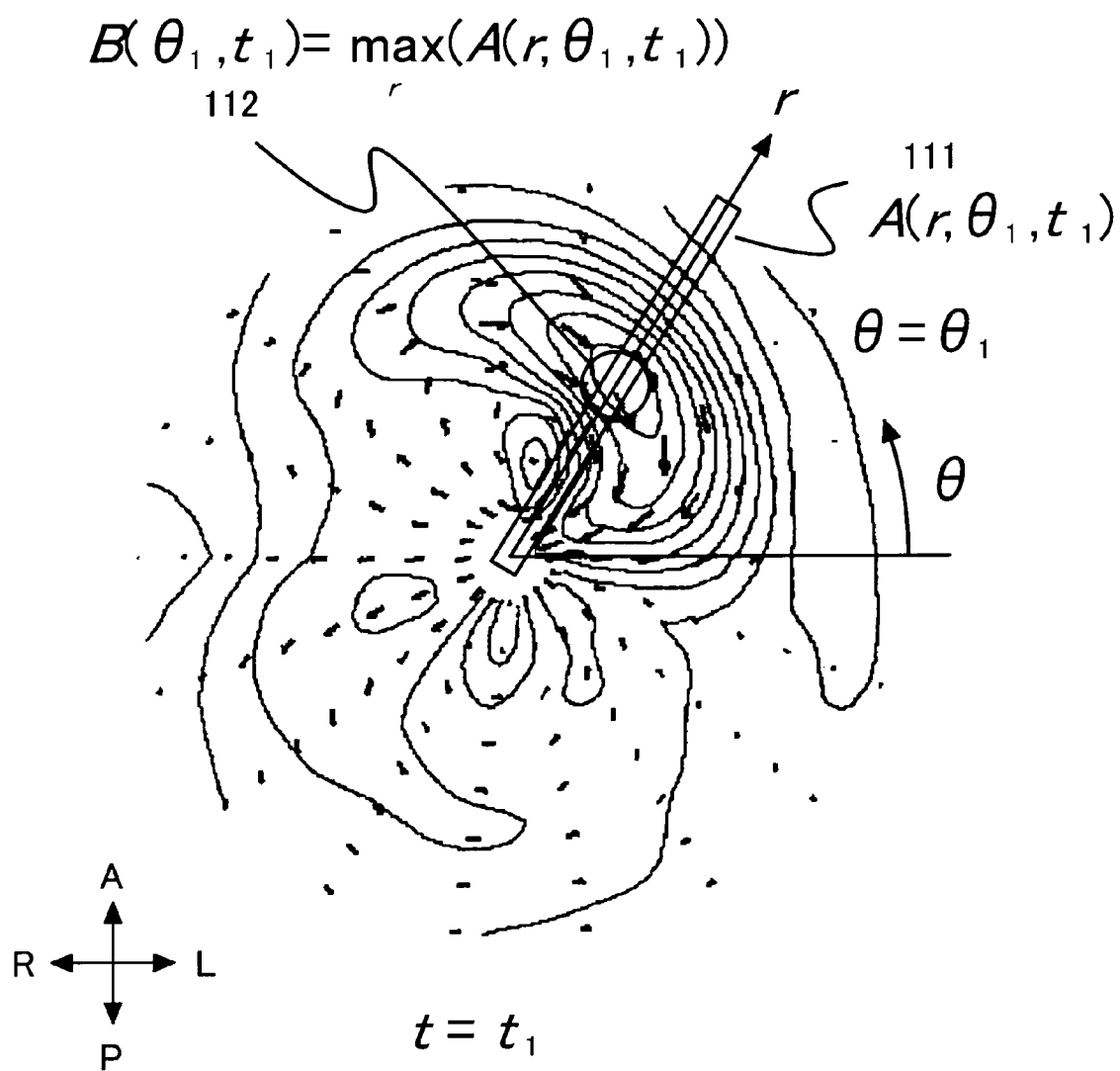
FIG. 13 illustrates a new displaying method obtained on the basis of a planispheric chart in the embodiment of the present invention.

FIG. 13 shows a chart for describing a new displaying method obtained on the basis of planispheric charts in this embodiment of the present invention according to the CAM examples displayed on the planispheric chart 92-9 in a time band 91 of a QRS complex waveform shown in FIG. 11.

As described above, each CAM displayed on a planispheric chart at a point of time t can show a distance r from the lower tip part (apex cordis) of the subject heart, a function of the deflection angle θ, and A (r,θ,t). As shown in the example in FIG. 13, the value of A (r, θ,t) at a point of time t, at a deflection angle θ=θ1, and at a radius vector r is A (r,θ1,t1) 111. When finding a radius vector r=rmax at which the absolute value of the current vector of A (r,θ1,t1) becomes the maximum, the maximum value 112 of the absolute value of the current vector is B(θ1, t1)=max{A (r, θ1, t1)}=A(rmax, θ1, t1).

When finding a radius vector r=rmax at which the absolute value of the current vector of A (r,θ,t) becomes the maximum at a defection angle θ and at a point of time t, the maximum value of the absolute value of the current vector is B(θ,t)=max{A(r,θ,t)=A (rmax,θ,t). Consequently, it is possible to obtain the maximum value of the absolute value of the current vector on a radius vector r at a deflection angle θ and at a point of time t according to the B (θ,t), then the variable r of the A (r,θ,t) is represented by rmax to reduce the number of dimensions and obtain a function assuming both deflection angle θ and point of time t as variables and B (θ,t). It is thus possible to create a new map for displaying changes of this B (θ,t) with time.

Figure 14:
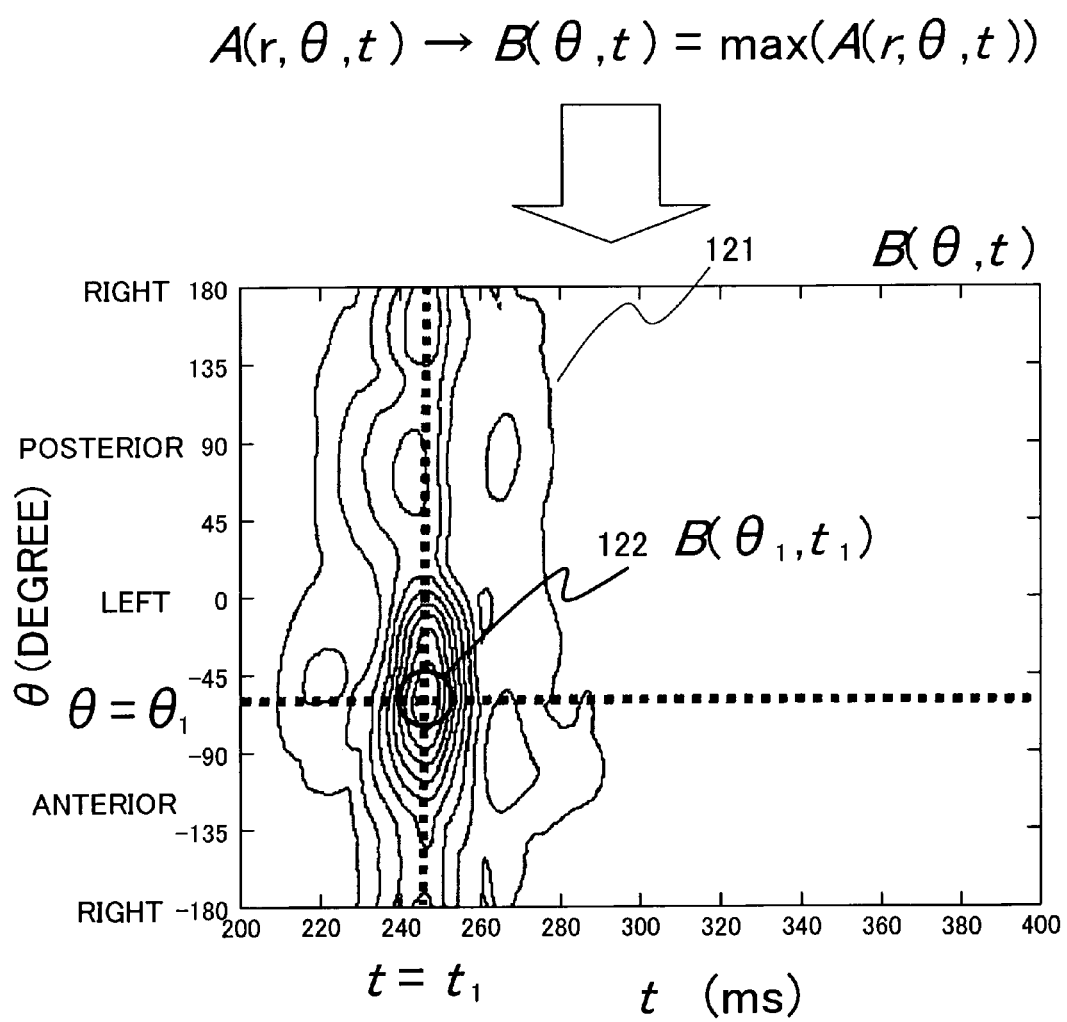
FIG. 14 illustrates a new map displayed as a contour map for changes of both deflection angle and time of B (θ,t) obtained on the basis of a planispheric chart A (r,θ,t) in the embodiment of the present invention.

FIG. 14 shows a chart for describing an example of how the new map 121 displays changes of both deflection angle and time of B (θ,t) obtained on the basis of the planispheric chart A (r,θ,t) in the example of the present invention with a contour map. In other words, the map 121 is a contour map in which points having the same B(θ,t)=max {A (r,θ,t)=A(rmax,θ,t) are connected. The B (θ,t) shown in the map 121 takes the maximum value B(θ1,t1) 122 at a point (θ1,t1) in shown FIG. 13.

In FIG. 14, "Left", "Right", "Anterior", and "Posterior" are displayed to make it easier to understand the displayed items. The "Left" denotes the left side of an object heart, the "Right" denotes the right side of the heart, the "Anterior" denotes the front side of the heart, and the "Posterior" denotes the back side of the heart. And, the map 121 shown in FIG. 14 is used to observe changes of the state of the subject heart with time easily, that is, in which of the right side and the left side at the front side (anterior side) of the subject heart, strong heart electrical excitement is recognized, as well as in which of the right side and the left side at the back side of the heart, strong electrical excitement is recognized.

Although a contour chart in which points having the same B(θ,t)=max{A(r,θ,t)}=A(rmax,θ,t) are connected is found in the examples shown in FIGS. 13 and 14, points having the same B(θ,t)=Σ{A (r,θ,t)=Σ{A (r,θ,t)} or B (θ,t)=Σ{A (r,θ,t)}/ N may be connected in the contour chart by assuming that the addition symbol Σ denotes that measuring is to be done at every measuring point (including virtual ones) on a radius vector r, that is, at every N point.

Hereunder, effects to be obtained with use of actually measured data shown in FIGS. 15 and 16 will be described with reference to some concrete examples of measurement results in this embodiment of the present invention.

FIG. 15 is a graph of a normal case obtained from a healthy person and FIG. 16 shows a graph of a patient with right-bundle branch block.

Figure 15A:
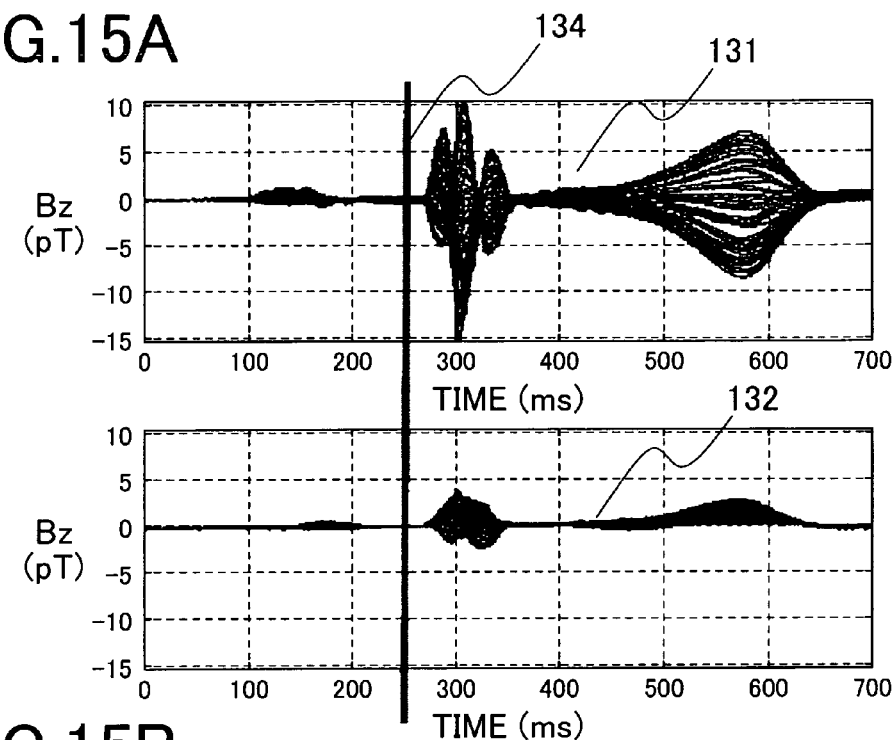
FIG. 15 illustrates graphs of a magnetocardiogram related to a normal case and B (θ,t) obtained in the embodiment of the present invention.

FIG. 15A shows a graph of an example of a magnetocardiogram waveform of a normal example (healthy person), measured with magnetic sensors of 64 channels disposed in an 8×8 square grid pattern on a plane composed just like that in FIGS. 8A and 8B. The graph denotes that the magnetocardiogram waveforms 131 and 132 measured with each of the magnetic sensors of 64 channels are superposed in the display.

Each of the horizontal axes of the magnetocardiogram waveforms 131 and 132 measured at the front and back side measuring positions denotes a point of time (ms) to which points of time are adjusted for position with reference to the R wave peak point of time in the second inductive electrocardiogram measured simultaneously at the same electrode position as that of the magnetocardiogram waveforms of the back and front side measuring positions just like in FIGS. 8A and 8B. The vertical axis in FIG. 15A denotes the intensity (pT) of the magnetocardiogram waveform. A line 134 vertical to the horizontal axis shown in FIG. 15A denotes a point of time for starting display of mapping data with a contour chart of B (θ, t).

Figure 15B:
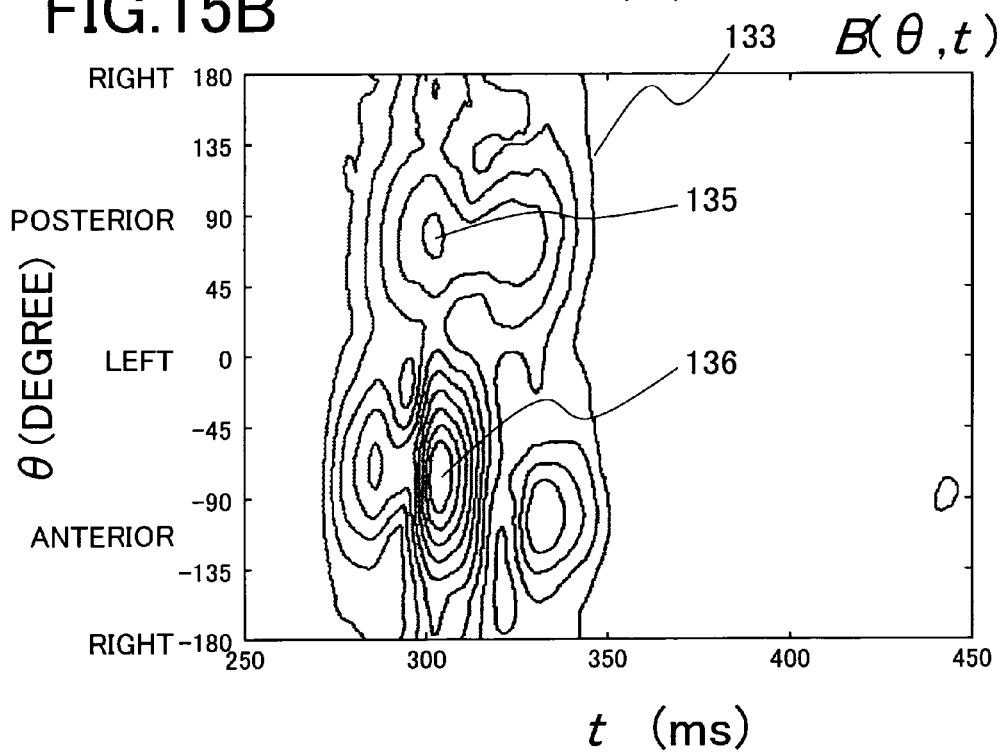

FIG. 15B shows changes of B(θ,t)=max {A(r,θ,t)}=A (rmax,θ,t) with time started at the display starting point of time 134 (250 ms: Q on setting time) with a contour map (map B(θ,t)) 133. The difference between the maximum peak value 136 at the front side (between 0° and 180°) and the maximum peak value 135 at the back side (between 0° and 180°) is about 8 ms, which can be almost ignored.

Figure 16A:
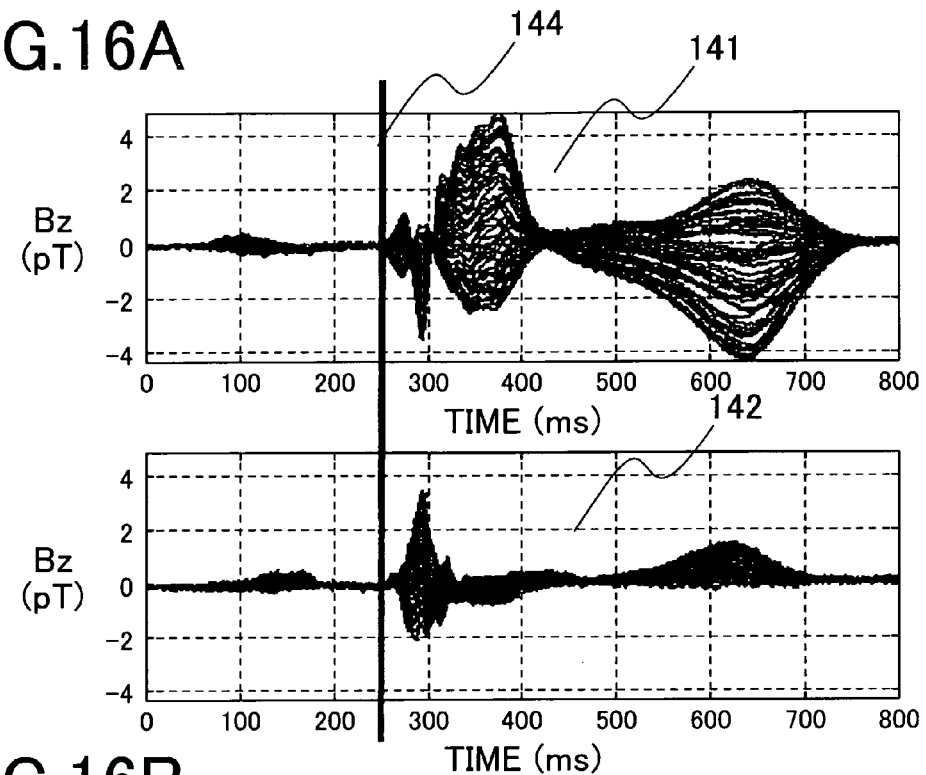
FIG. 16 illustrates graphs of a magnetocardiogram related to a patient with right-bundle branch block and B (θ,t) obtained in the embodiment of the present invention.

FIG. 16A shows a magnetocardiogram waveform of a patient with right-bundle branch block, measured on the same condition as that of FIG. 15A. The magnetocardiogram waveform 141 measured at the front side measuring position and the magnetocardiogram waveform 142 measured at the back side measuring position are denoted by a time axis (ms) at which the positions of the waveforms 141 and 142 are adjusted with reference to the point of time of the R wave peak of the second inductive electrocardiogram measured simultaneously at the position of the same electrode just like in FIGS. 8A and 8B. The vertical axis in FIG. 16A denotes the intensity (pT) of the magnetocardiogram waveform. And similarly to FIG. 15A, a line 144 vertical to the horizontal axis shown in FIG. 16A denotes a point of time for starting display of mapping data with a contour chart of B(θ,t).

Figure 16B:
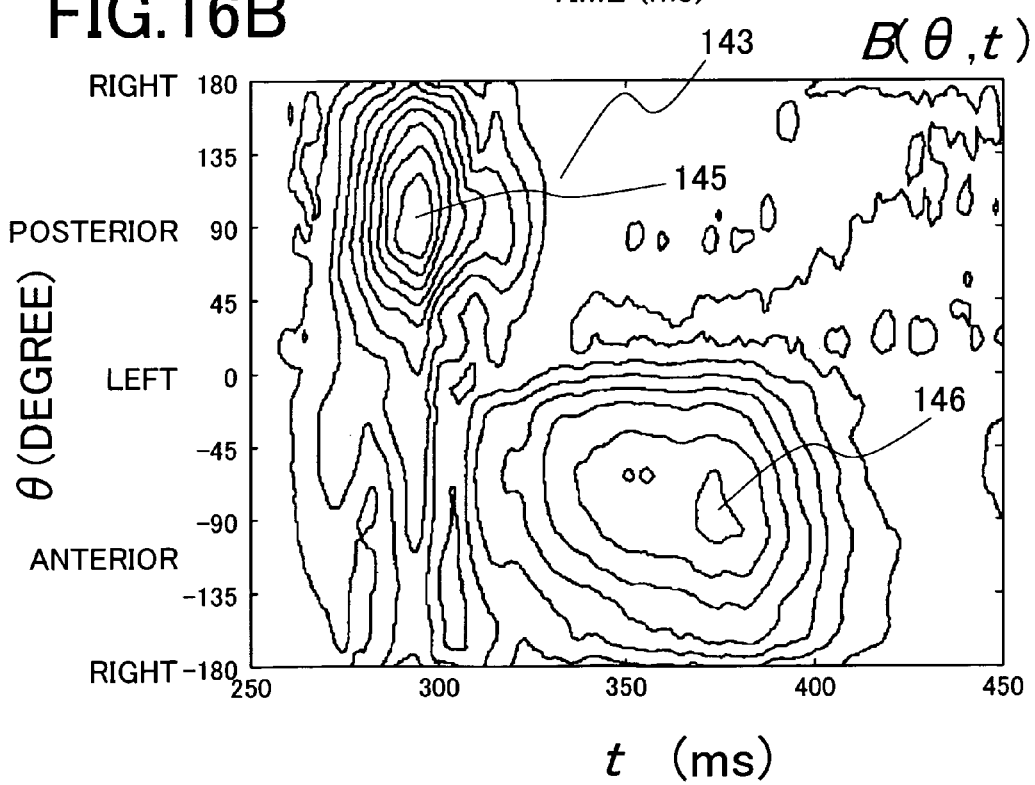

Just like FIG. 15A, the B (θ,t) shown in FIG. 16B is shown as changes with time started at the display starting time line 144 (250 ms: Q on-setting time) and the difference between the point of time of the maximum peak value 146 at the front side (0° to −180°) and the point of time of the maximum peak value 145 at the back side (0° to 180°) is about 80 ms, which is clearly about 10 times longer than the difference (about 8 ms) detected from the healthy person shown in FIG. 15B.

In FIGS. 13 through 16, a description has been made for a case in which B(θ,t) obtained from A(r,θ,t) is displayed, but another new map (a time-delay map) created for the A (r,θ,t) may be displayed.

Figure 18:
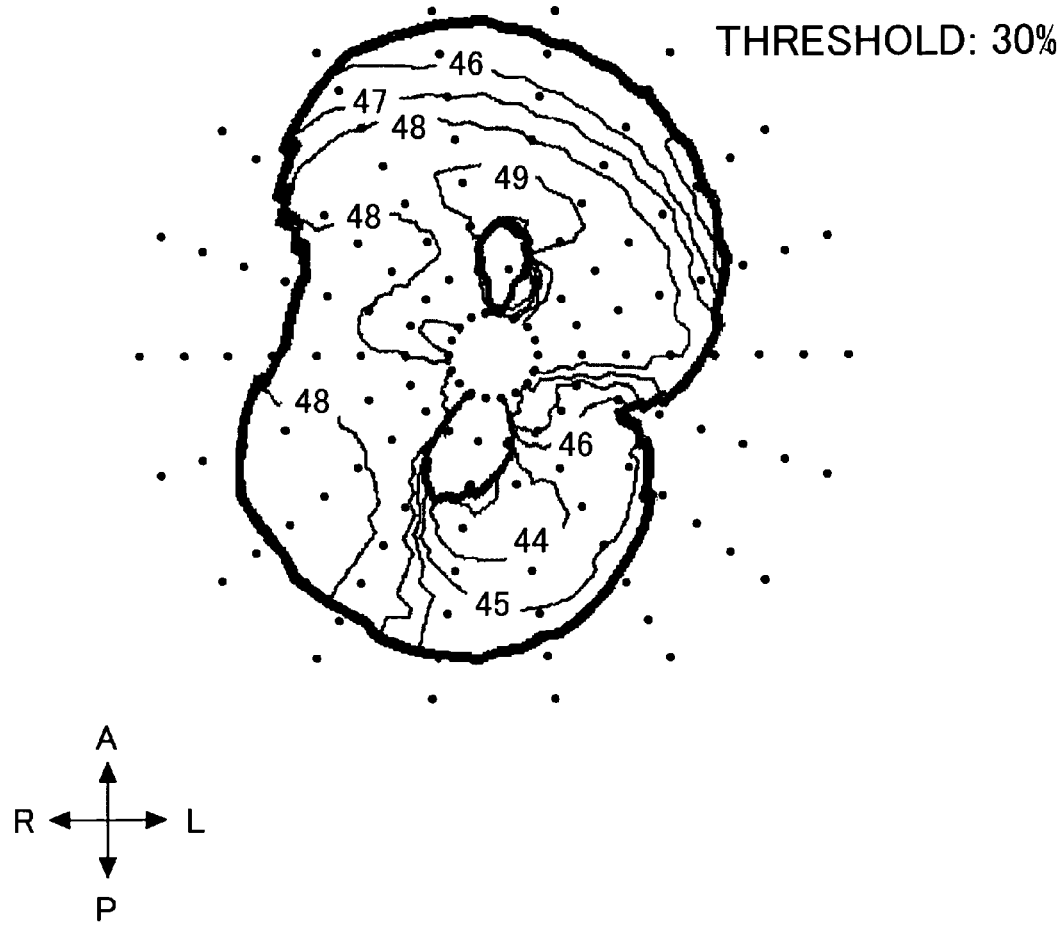
FIG. 18 illustrates a time-delay map obtained from the healthy person in the normal case shown in FIG. 15 and displayed as a planispheric chart.
Figure 19:
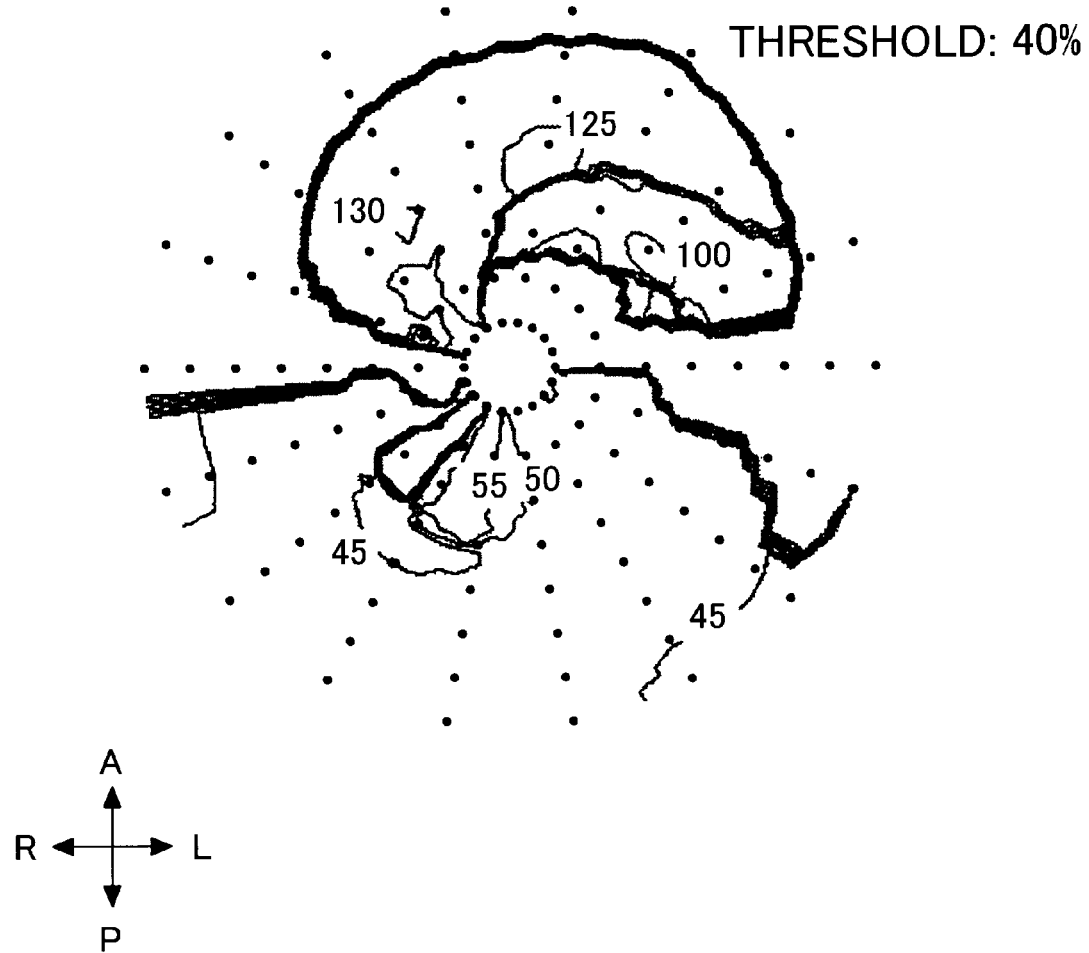
FIG. 19 illustrates a time-delay map obtained from the patient with right-bundle branch block shown in FIG. 16 and displayed as a planispheric chart.

Hereunder, a description will be made for an embodiment for creating a time-delay map with reference to FIGS. 17 through 19. In FIGS. 18 and 19, each dot denotes a measuring point and each value in FIGS. 18 and 19 denotes a time delay value.

Figure 17:
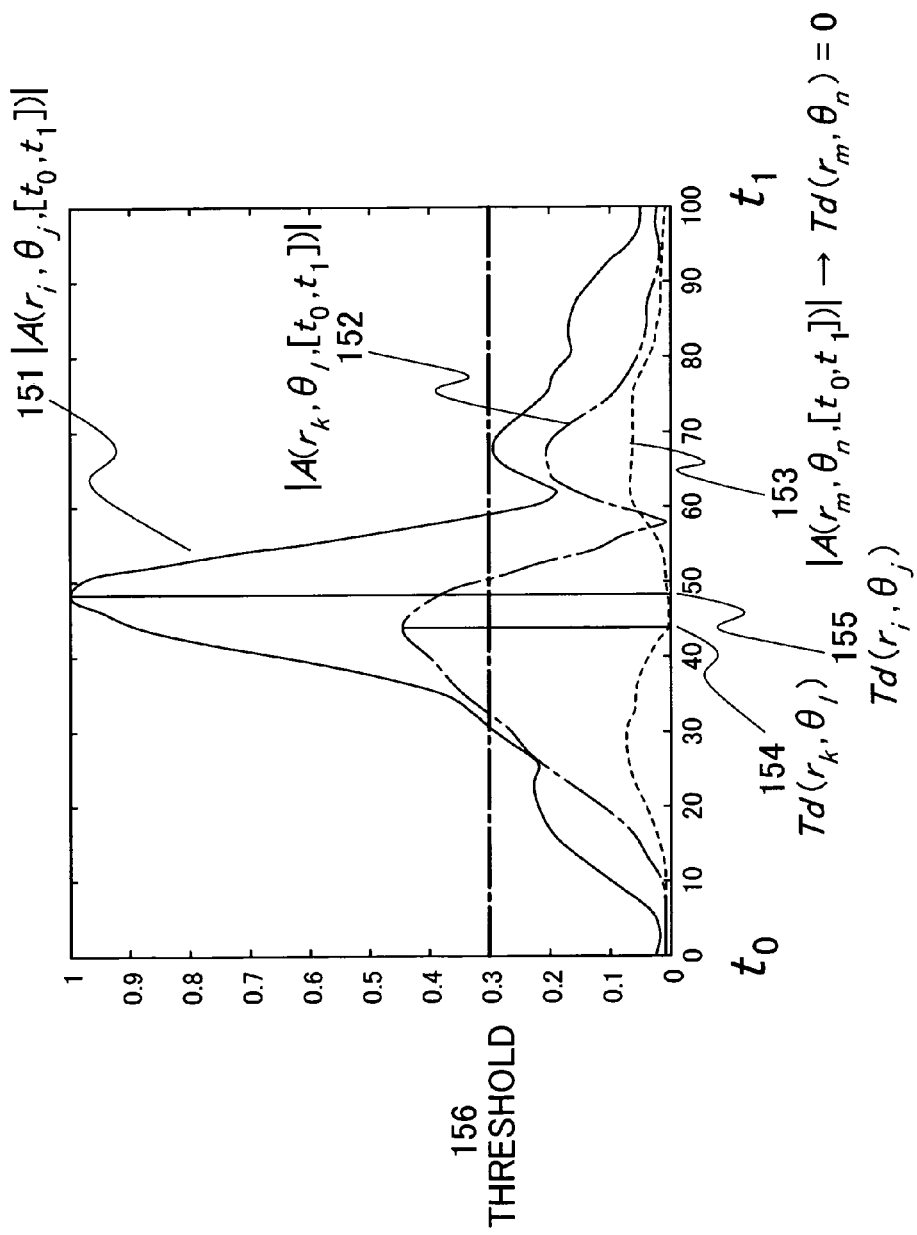
FIG. 17 illustrates how to create a time-delay map in the embodiment of the present invention.

FIG. 17 shows a chart for describing how to create a time delay map. FIG. 17 shows an example of changes of a CAM with time displayed on a planispheric chart in a time section [t0,t1]. In FIG. 17, the time section [t0,t1] denotes a time band 91 of the QRS complex waveform in each of the magnetocardiogram waveforms 61 and 62 shown in FIG. 11.

Hereunder, changes of the A (r,θ,t) with time at a deflection angle θ, at a radius vector r, and at a point of time t in a time section [t0,t1] is examined. In other words, changes of the CAM displayed on a planispheric chart with time in a time section [t0,t1] is examined. FIG. 17 shows the absolute value of a current vector, a waveform of $|I|=\sqrt{(Ix2+Iy2)}=|A(r,\theta,t)|$, and a time delay $Td(r,\theta)$.

As a typical example, on the screen are displayed $|A(ri,\theta j[t0,t1])|$(a waveform 151), $|A(rk,\theta 1[t0,t1])|$(a waveform 152), $|A (rm, \theta n, [t0, t1])|$(waveform 153), and a time delay Td (ri,θj)(a time delay 155), Td(rk, θ1)(a time delay 154), Td(rm,θn) at the three points (ri,θj), (rk,θ1), and (rm,θn) selected from the measuring points on a planispheric chart. In FIG. 17, the waveform $|A (r,\theta,[t0,t1])|$ to be displayed is normalized by assuming the maximum value of the waveform 151 as 1.

A threshold value (Athr) 156 is set beforehand for a waveform $|A(r, \theta, t)|$ and a point of time tmax that provides the maximum value of $|A(r, \theta, [t0, t1])|$ that satisfies $|A(r,\theta,[t0,t1])| \geq Athr$ is set as a time-delay $Td(r, \theta)$=tmax. Then, in case $|A(r, \theta, [t0, t1])|<Athr$ is satisfied at every point of time in the time section [t0,t1], the time-delay is assumed to be $Td(r, \theta)$=0. The threshold value (Athr) 156 set as described above is effective to reduce the influence by low amplitude noise contained in $|A(r, \theta, [t0, t1])|$.

In the example shown in FIG. 17, Td(ri, θj)=45 ms (a time delay 155), Td(rk, θ1)=48 ms (a time delay 154), and Td(rm, θn)=0 are satisfied. With the above processings, a time delay $Td(r,\theta)$ at each coordinate (measuring) point (r, θ, [t0, t1]) is obtained.

As described above, the present invention makes it possible to set a threshold value (Athr), find t=tmax that provides the maximum $\{|A(r, \theta, [t0, t1])|\}$ that satisfies $|A(r, \theta, [t0, t1])| \geq Athr$, show a change of $|A(r, \theta, t)|$ at a point of time t in a time section [t0, t1] with tmax to display a time delay $Td(r, \theta)$, reduce the number of dimensions, obtain a function that assumes a deflection angle θ and a point of time t as variables, and Td (r, θ). A new map for displaying changes of this Td(θ, t) with time is thus created. The obtained time-delay map $Td(r, \theta)$ is displayed as a planispheric chart as shown in FIGS. 18 and 19 to be described later.

FIG. 18 shows a time-delay map $Td(r,\theta)$ obtained from the healthy person shown in FIG. 15 as a planispheric chart (the threshold value (Athr) is assumed as 0.3 (30%).)

In FIG. 18, the time-delay map $Td(r,\theta)$ is displayed with a contour map in which points having the same time-delay value are connected (similarly to FIG. 19 to be described). As to be understood clearly, the time-delay at each measuring point on the planispheric chart is within 44 ms to 49 ms, but almost no difference is recognized in such a time-delay between measuring points.

FIG. 19 shows a planispheric chart obtained from a time-delay map Td(r, θ) with respect to the patient with right-bundle branch block shown in FIG. 16 (the threshold value (AThr) is assumed as 0.4 (40%) here.)

In the time-delay map of the patient with right-bundle branch block shown in FIG. 19, the time delay at the back side is about 45 ms to 55 ms while that at the front side is found to be as much as 130 ms partially. Because such a large time delay is found at a position in the right-bundle branch block, the position might thus denote occurrence of a fault in the stimulus transmission system.

The difference of about 80 ms between a point of time 130 ms at which the longest time delay is detected and an average value 50 ms of time delays at the back side matches almost completely with the difference of about 80 ms between a point of time at which the maximum peak value 146 is detected at the front side and a point of time at which the maximum peak value 145 is detected at the back side. Finding a region in which such a time delay is detected might provide information effective to estimate regions of both right and left ventricles to be treated with pacing, for example.

The time-delay map described above is not necessarily displayed as one planispheric chart with polar coordinates. For example, rectangular coordinates to show any of the front side measuring position 21 and the back side measuring position 22 may be used to display the time-delay maps shown in FIGS. 18 and 19 separately for the front side and for the back side.

Figure 20:
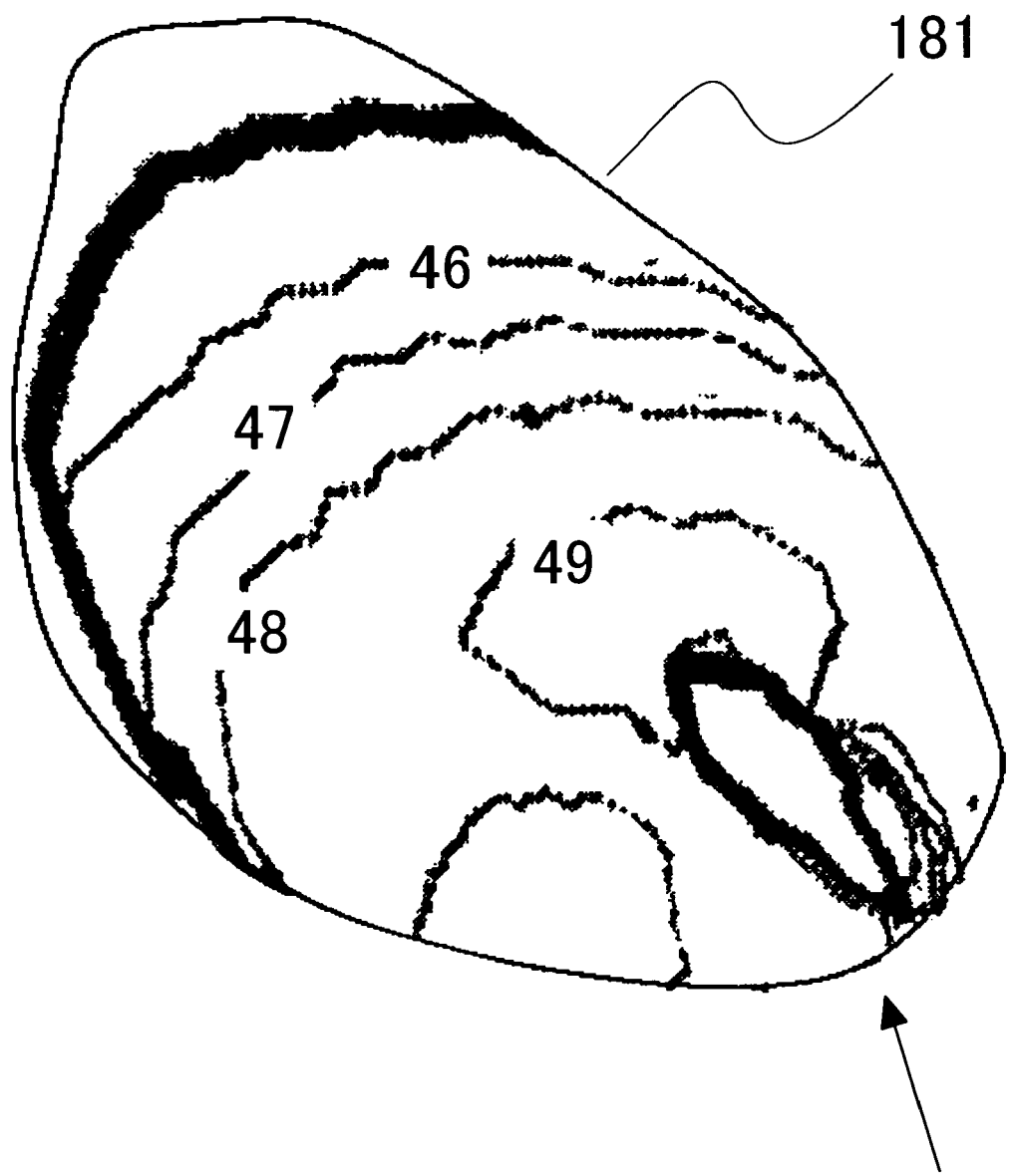
FIG. 20 illustrates a time-delay map of the healthy person shown in FIG. 18, which is displayed on a 3-dimensional heart model in the embodiment of the present invention.

Hereunder, a description will be made for another embodiment for projecting and displaying a time-delay map $Td(r,\theta)$ on a 3-dimensional heart model with reference to FIGS. 20 and 21. FIG. 20 shows a time-delay map (Athr (threshold value)=0.3 (30%)) shown in FIG. 18 on a 3-dimensional heart model 181 and FIG. 21 shows a time-delay map (Athr (threshold value)=0.4 (40%)) related to a patient with right-bundle branch block shown in FIG. 19 on a 3-dimensional heart model 191.

Figure 21:
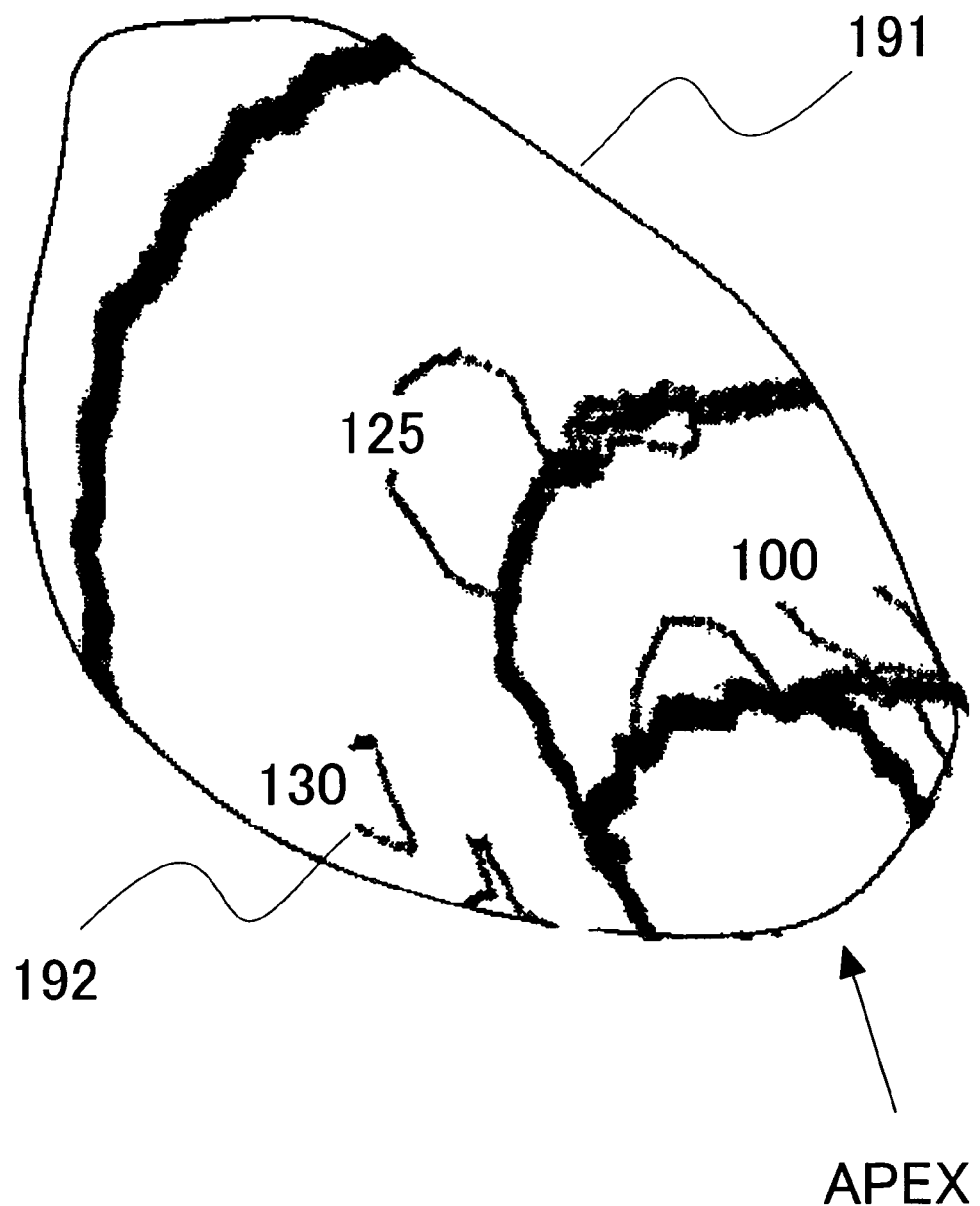
FIG. 21 illustrates a time-delay map related to the patient with right-bundle branch block shown in FIG. 19 and displayed on a 3-dimensional heart model in the embodiment of the present invention.

The values shown in FIGS. 20 and 21 denote time-delay values just like in FIGS. 18 and 19. The lower right tip region of the 3-dimensional heart model shown in FIGS. 18 and 19 is an apex cordis in the lower portion of the heart.

The 3-dimensional heart models 181 and 191 are represented by graphic data showing an external surface frame of a subject heart and displayed 3-dimensionally with a shadow on a display device. A time-delay map is projected on the external surface of the heart and superposed on the 3-dimensional heart model, so that the time-delay is visualized for easy observation.

In FIG. 21, it is recognized easily that a large time delay (130 ms) occurs in a region 192 and another time delay occurs in the lower part of the right ventricle. As shown clearly in the examples in FIGS. 20 and 21, it is easy to recognize such a time delay of electrical excitement visually.

Figure 22:
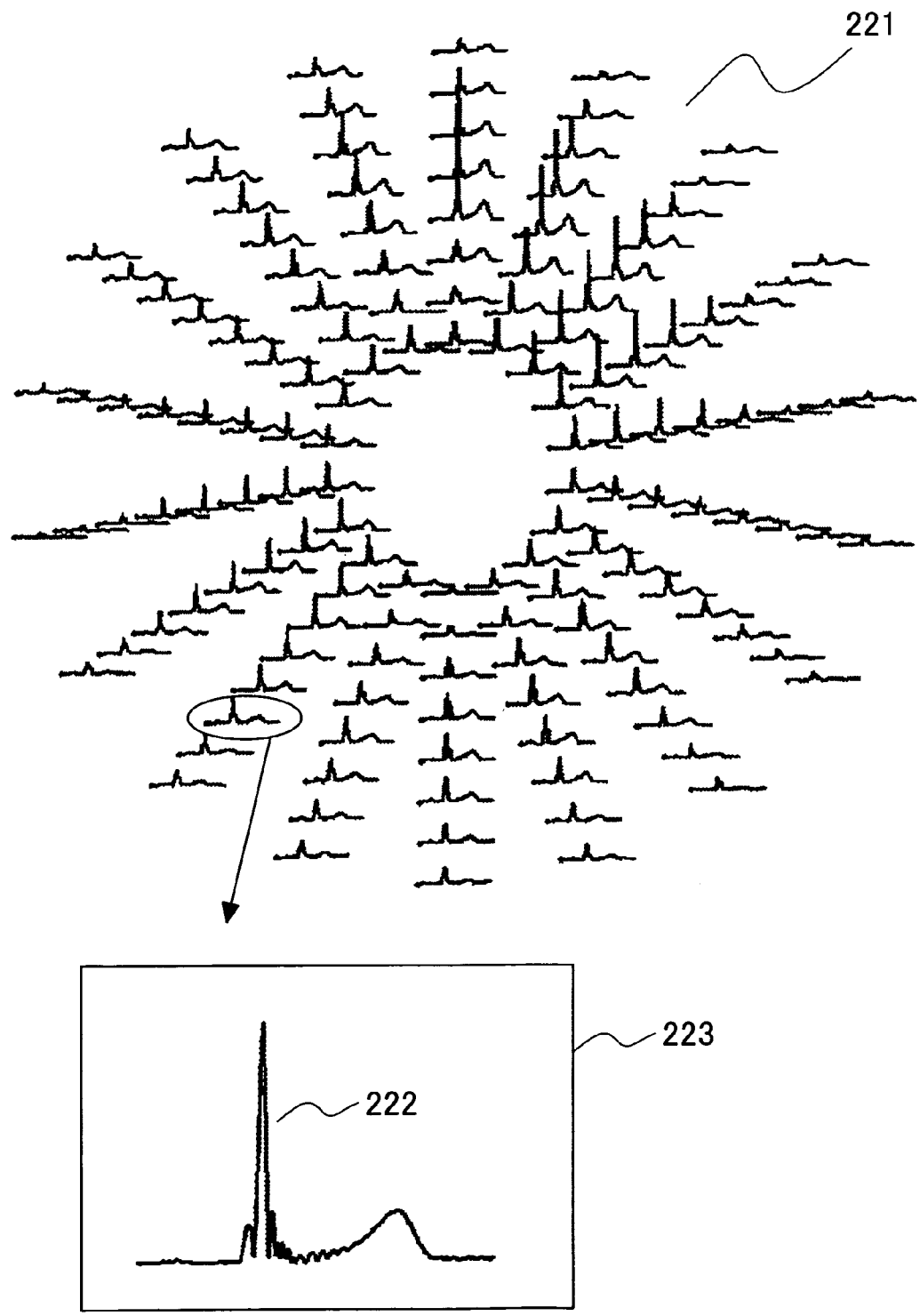
FIG. 22 illustrates how a waveform of the absolute value of a current vector changes with time using a planispheric chart in the embodiment of the present invention.

FIG. 22 shows a chart for describing an example for displaying a waveform that denotes changes of the absolute values (size and intensity) of a current vector with time on a planispheric chart by obtaining the absolute values of a pseudo current vector at a point of time t of each magnetocardiogram waveform measured from a healthy person at each measuring point.

FIG. 22 shows a waveform 221 for denoting changes of the absolute value of a current vector (the size of the current arrow at each measuring point) with time, obtained from the original magnetocardiogram waveform used to obtain a CAM instead of the CAM shown with a planispheric chart in FIGS. 10A, 11A, and 12A. In other words, in FIG. 22, the absolute values of the current vector at each point of time is displayed as time changes. The absolute values are obtained from the magnetocardiogram waveform at each measuring point of the front and back sides measured at both of the front side measuring position 21 and the back side measuring position 22. The waveform 221 is thus displayed as changes of the absolute values of the current vector with time, displayed on a planispheric chart.

Similarly, it is also possible to display a waveform for denoting changes of the absolute values of a current value with time, obtained from the original magnetocardiogram waveform used to find the time-delay map instead of the time-delay map shown with a planispheric chart in FIGS. 18 and 19.

The waveforms on the radius vectors A3 and C3 shown in the lower chart in FIG. 4 are obtained by calculating the waveform that denotes changes of the absolute values of a current vector with time multiplied by a weight coefficient α (calculated with the (expression 7)) in the (expression 8) and the (expression 9). The waveform is obtained from the magnetocardiogram waveform measured at the back side measuring position 22. It is also possible here not to display the waveforms on the radius vectors A3 and C3 while it is possible to display the waveform that denotes changes of the absolute values of the current vector obtained from the magnetocardiogram waveform measured at the back side measuring position 22 and multiplied by a weight coefficient α together with the waveform that denotes changes of the absolute values of the current vector with time, obtained from the magnetocardiogram waveform measured at the front side measuring position 21.

While FIG. 22 denotes a waveform that shows changes of a current arrow size with time on a planispheric chart, FIG. 22 may also display a magnetocardiogram waveform that denotes changes of a size of the measured magnetocardiogram with time similarly to the above case.

In case a waveform that denotes changes of the absolute value of a current vector with time or enlarged magnetocardiogram waveforms are to be displayed as shown in FIG. 22, the waveform at any measuring point on the planispheric chart may be selected to display the waveform 222 in which both intensity and time axes are expanded on the expanded display screen 223.

Because planispheric charts are used for displaying magnetocardiogram waveforms as described above, a waveform for denoting changes of the absolute values of a current vector or magnetocardiogram waveform is checked in detail and the relationship between CAM and time-delay map can be known more in detail.

According to the present invention, positions of a plurality of magnetic field sensors used to detect magnetic fields generated from a subject, as well as positions of measuring points at which the magnetic fields are detected from both front (anterior side) and back (posterior side) sides of the subject heart are converted to polar coordinates, thereby displaying a magnetocardiogram waveform and/or scalar value and/or vector value obtained from the magnetocardiogram waveform on a planispheric chart. Because one planispheric chart is used to display how the whole heart is excited electrically, the electrical excitement at both front and back sides of the subject heart can be observed at a time to easily find abnormality in the electrical excitement.

While a description has been for various kinds of methods for analyzing magnetocardiogram waveforms, as well as various kinds of methods for displaying analyzed data in examples of measurement of magnetocardiogram waveforms in the above embodiment of the present invention, it would be clear that those analyzing methods and displaying methods can also apply to measurement of magneto-encephalogram.

Second Embodiment

Hereunder, another (the second) embodiment of the present invention will be described with reference to the accompanying drawings.

1. According to the first aspect of the present invention, the biomagnetic measurement apparatus comprises a plurality of magnetic field sensors disposed two-dimensionally to detect a magnetic field from a subject respectively, an arithmetic processing unit for collecting the magnetic fields to be measured from the first and second directions of the subject as first and second magnetic field data to process their data arithmetically, and a display device for displaying a result of the arithmetic processing.

The first direction is a direction from the thoracic (front) side of the subject and the second direction is a direction from the back side of the subject.

The arithmetic processing is executed to convert each of the positions of the plurality of magnetic field sensors to polar coordinates represented by a radius vector r and an oblique angle $\theta$ respectively within the first range in which the oblique angle $\theta$ is $0°<\theta<180°$ when detecting the magnetic fields from the first direction and within the second range in which the oblique angle $\theta$ is $180°<\theta<360°$ when detecting the magnetic fields from the second direction, then the first magnetic field data is set to correspond to the polar coordinate within the first range and the second magnetic field data is set to correspond to the polar coordinate within the second range, thereby by combining data of the first and second magnetic fields to obtain data of the third magnetic field at the polar coordinates within the third range in which the oblique angle $\theta$ is $\theta=0°$ and $\theta=180°$.

2. According to the second aspect of the present invention, the biomagnetic measurement apparatus comprises a plurality of magnetic field sensors disposed two-dimensionally to detect a magnetic field from a subject respectively, an arithmetic processing unit for collecting the magnetic fields to be measured from the first and second directions of the subject as the first and second magnetic fields to process their data arithmetically, and a display device for displaying a result of the arithmetic processing.

The first direction is a direction from the thoracic (front) side of the subject and the second direction is a direction from the back side of the subject;

The arithmetic processing is executed to convert each of the positions of the plurality of magnetic field sensors to polar coordinates represented by a radius vector r and an oblique angle $\theta$ respectively within the first range in which the oblique angle $\theta$ is $0°<\theta<180°$ when detecting the magnetic fields from the first direction and within the second range in which the oblique angle $\theta$ is $180°<\theta<360°$ when detecting the magnetic fields from the second direction, then the first magnetocardiogram data or value obtained from the first magnetocardiogram data is set to correspond to the polar coordinates within the first range and the second magnetocardiogram data or value obtained from the second magnetocardiogram is set to correspond the polar coordinates within the second range, thereby displaying one planispheric chart that displays the first magnetocardiogram data or value obtained from the first magnetocardiogram data and the second magnetocardiogram data or value obtained from the second magnetocardiogram on the display device.

3. According to the third aspect of the present invention, the biomagnetic measurement apparatus comprises a plurality of magnetic field sensors disposed two-dimensionally to detect a magnetic field from a subject respectively, an arithmetic processing unit for collecting the magnetic fields to be measured from the first and second directions of the subject as the first and second magnetic fields to process their data arithmetically, and a display device for displaying a result of the arithmetic processing.

The arithmetic processing is executed to convert each of the positions of the plurality of magnetic field sensors to polar coordinates represented by a radius vector r and an oblique angle $\theta$ respectively within the first range in which the oblique angle $\theta$ is $0°<\theta<180°$ when detecting the magnetic fields from the first direction and within the second range in which the oblique angle $\theta$ is $180°<\theta<360°$ when detecting the magnetic fields from the second direction, then the first magnetic field data is set to correspond to the polar coordinates within the first range and the second magnetic field data is set to correspond to the polar coordinates within the second range, thereby obtaining a planispheric chart to be displayed on the display device.

4. According to the fourth aspect of the present invention, the method for displaying data of the first and second magnetocardiograms generated from a subject's heart and measured from the first and second directions of the subject, then collected in a memory.

The first direction is a direction from the thoracic (front) side of the subject and the second direction is a direction from the back side of the subject.

Then, each of the positions of the plurality of magnetic field sensors is converted to polar coordinates represented by a radius vector r and an oblique angle θ within the first range in which the oblique angle is 0°<θ<180° when detecting the magnetic fields from the first direction and within the second range in which the oblique angle θ is 180°<θ<360° when detecting the magnetic fields from the second direction, then the first magnetic field data is set to correspond to the polar coordinates within the first range and the second magnetic field data is set to correspond to the polar coordinates within the second range, then the first and second magnetocardiogram data are set to correspond to a coordinate point (assumed as (r,θ,t) while t denotes a point of time on the time axis of the magnetocardiogram waveform) to display the planispheric chart that denotes distribution of current vectors (assumed as A (r,θ,t)) obtained from the magnetocardiogram data corresponding to the coordinate point (r,θ,t) on the display device.

5. According to the fifth aspect of the present invention, the method for displaying biomagnetic field data according to claim 4 sets the third magnetocardiogram data obtained by multiplying the second magnetocardiogram data by a predetermined value to correspond to the polar coordinates within the second range instead of the second magnetocardiogram data and sets the first and third magnetocardiogram data to correspond to a coordinate point (r, θ, t), thereby the planispheric chart that denotes distribution of current vectors (assumed as A (r, θ, t)) obtained from the magnetocardiogram data corresponding to the coordinate point (r, θ, t) is displayed on the display device.

6. According to the sixth aspect of the present invention, the method for displaying biomagnetic field data according to claim 4 sets the third magnetocardiogram data obtained by dividing the first magnetocardiogram data by a predetermined value to correspond to the polar coordinates within the first range instead of the first magnetocardiogram data and sets the first and third magnetocardiogram data to correspond to a coordinate point (r, θ, t), thereby the planispheric chart that denotes distribution of current vectors (assumed as A (r, θ, t)) obtained from the magnetocardiogram data corresponding to the coordinate point (r, θ, t) is displayed on the display device.

7. According to the seventh aspect of the present invention, the method for analyzing data of the first and second magnetocardiograms measured from the first and second directions of a subject with use of a plurality of magnetic field sensors displayed two-dimensionally and collected in a memory as data of the first and second magnetocardiograms.

The first direction is a direction from the thoracic (front) side of the subject, the second direction is a direction from the back side of the subject. Then, each of positions of the plurality of magnetic field sensors is converted to polar coordinates represented by a radius vector r and an oblique angle θ respectively within the first range in which the oblique angle is 0°<θ<180° when detecting the magnetocardiograms from the first direction and within the second range in which the oblique angle θ is 180°<θ<360° when detecting the magnetocardiogram from the second direction, then the first magnetocardiogram data is set to correspond to the polar coordinates within the first range, the second magnetocardiogram is set to correspond to the polar coordinates within the second range, then the third magnetocardiogram data within the third range in which the oblique angle θ is θ=0° and θ=180° is obtained by combining data of the first and second magnetocardiograms, the third magnetocardiogram data is then set to correspond to the polar coordinates within the third range, data of the first to third magnetocardiograms are set to correspond to a coordinate point (assumed as (r, θ, t) and t denotes a point of a time axis of the magnetocardiogram waveform) on a planispheric chart represented by the polar coordinates to obtain a current vector (assumed as A (r, θ, t)) from the magnetocardiogram data corresponding to the coordinate point (r, θ, t).

According to the present invention, it is possible to provide a biomagnetic measurement apparatus capable of observing the electrical excitement in the whole subject heart at a time to know the state, thereby finding abnormality in the electrical excitement easily.

What is claimed is:

1. A biomagnetic measurement apparatus, comprising:
a plurality of magnetic field sensors disposed two-dimensionally to detect a magnetic field from an inspection object respectively;
an arithmetic processing unit for collecting said magnetic fields to be measured from first and second directions of said inspection object to process their data arithmetically; and
a display device for displaying a result of said arithmetic processing,
wherein said arithmetic processing is executed to convert each of the positions of said plurality of magnetic field sensors to polar coordinates represented by a radius vector r and an oblique angle respectively within a first range in which said oblique angle θ is 0°<θ<180° when detecting said magnetic fields from said first direction and each of the positions of said plurality of magnetic field sensors to polar coordinates within a second range in which said oblique angle θ is 180°<θ<360° when detecting said magnetic fields from said second direction, then set said first magnetic field data to correspond to said polar coordinates within said first range and said second magnetic field data to correspond to said polar coordinates within said second range, and combine data of said first and second magnetic fields to obtain data of a third magnetic field at polar coordinates within a third range in which said oblique angle θ is θ=0° and θ=180°.

2. The biomagnetic measurement apparatus according to claim 1,
wherein said arithmetic processing for combining magnetic field data includes a first interpolating processing to obtain data of said third magnetic field at said polar coordinate within said third range in which said oblique angle θ is θ=0° with use of said first and second magnetic field data at said oblique angle θ that gets closest to θ=0° and a second interpolating processing to obtain said third magnetic field data at said polar coordinate within said third range in which said oblique angle θ is θ=180° with use of data of said first and second magnetic fields at said oblique angle θ that gets closest to θ=180°.

3. The biomagnetic measurement apparatus according to claim 2,
wherein a weight coefficient is used for both of said first and second interpolating processings respectively.

4. A biomagnetic measurement apparatus, comprising:
a plurality of magnetic field sensors disposed two-dimensionally to detect a magnetic field from an inspection object respectively;
an arithmetic processing unit for collecting said magnetic fields to be measured from first and second directions of said inspection object as first and second magnetic field data to process their data arithmetically; and
a display device for displaying a result of said arithmetic processing,
wherein said arithmetic processing is executed to convert each of the positions of said plurality of magnetic field sensors to polar coordinates represented by a radius vector r and an oblique angle respectively within a first range in which said oblique angle θ is 0°<θ<180° when detecting said magnetic fields from said first direction and each of the positions of the plurality of magnetic field sensors to polar coordinates within a second range in which said oblique angle θ is 180°<θ<360° when detecting said magnetic fields from said second direction, then set said first magnetic field data to correspond to said polar coordinates within said first range, then set said second magnetic field data to correspond to said polar coordinates within said second range, and combine data of said first and second magnetic fields to obtain data of a third magnetic field at polar coordinates within said third range in which said oblique angle θ is θ=0° and θ=180° and set data of said third magnetic field to said polar coordinates within said third range and set said first to third magnetic field data to correspond to a coordinate point on a planispheric chart represented by said polar coordinates to obtain a scalar value and/or vector value from said magnetic field data at said coordinate point on said planispheric chart by an arithmetic processing, thereby displaying said planispheric chart that denotes distribution of said scalar value and/or vector value on said display device.

5. The biomagnetic measurement apparatus according to claim 4,
   wherein said arithmetic processing for combining magnetic field data includes a first interpolating processing to obtain data of said third magnetic field at said polar coordinates within said third range in which said oblique angle θ is θ=0° with use of said first and second magnetic field data at said oblique angle θ that gets closest to θ=0° and a second interpolating processing to obtain said third magnetic field data at said polar coordinates within said third range in which said oblique angle θ is θ=180° with use of data of said first and second magnetic fields at said oblique angle θ that gets closest to θ=180°.

6. The biomagnetic measurement apparatus according to claim 5,
   wherein a weight coefficient is used for both of said first and second interpolating processings respectively.

7. The biomagnetic measurement apparatus according to claim 4,
   wherein said first and second magnetic field data corresponding to said coordinate point is displayed on said display device together with said planispheric chart.

8. The biomagnetic measurement apparatus according to claim 4,
   wherein said magnetic fields measured by said plurality of magnetic field sensors are generated from the heart of said inspection object, said first direction is a direction from the thoracic (front) side of said inspection object, said second direction is a direction from the back side of said inspection object, and said vector value is a current vector obtained from said magnetocardiogram.

9. The biomagnetic measurement apparatus according to claim 4,
   wherein said magnetic fields measured by said plurality of magnetic field sensors are generated from the heart of said inspection object, said first direction is a direction from the thoracic (front) side of said inspection object, said second direction is a direction from the back side of said inspection object, said vector value is a current vector obtained from said magnetocardiogram, and said current vector is displayed as a change of said planispheric chart with time, and said current vector is displayed at said coordinate point.

10. The biomagnetic measurement apparatus according to claim 4,
    wherein said magnetic fields measured by said plurality of magnetic field sensors are generated from the heart of said inspection object, said first direction is a direction from the thoracic (front) side of said inspection object, said second direction is a direction from the back side of said inspection object, and said scalar value is the maximum value of a waveform of said magnetocardiogram in a predetermined time band or integral value in said time band.

11. The biomagnetic measurement apparatus according to claim 4,
    wherein all of said first to third magnetic field data are disposed at equal intervals at both of said radius vector and said oblique angle θ.

12. A biomagnetic measurement apparatus, comprising:
    a plurality of magnetic field sensors disposed two-dimensionally to detect a magnetic field from an inspection object respectively;
    an arithmetic processing device for collecting said magnetic fields to be measured from first and second directions of said inspection object as first and second magnetic field data to process their data arithmetically; and
    a display device for displaying a result of said arithmetic processing,
    wherein said first direction is a direction from the thoracic (front) side of said inspection object and said second direction is a direction from the back side of said inspection object;
    wherein said arithmetic processing is executed to convert each of the positions of said plurality of magnetic field sensors to coordinates represented by a radius vector and an oblique angle θ respectively within a first range in which said oblique angle θ is 0°<θ<180° when detecting said magnetic fields from said first direction and each of the positions of the plurality of magnetic field sensors to polar coordinates within a second range in which said oblique angle θ is 180°<θ<360° when detecting said magnetic fields from said second direction, then set said first magnetic field data to correspond to said polar coordinate within said first range and said second magnetic field data to correspond to said polar coordinate within said second range, and combine data of said first and second magnetic fields to obtain data of a third magnetic field at polar coordinates within said third range in which said oblique angle θ is θ=0° and θ=180°, then set said third magnetic field data to correspond to said polar coordinate within said third range and data of said first to third magnetic fields to correspond to a coordinate point (assumed as (r, θ, t) while the t denotes a point of time of a time axis of said magnetocardiogram) on a planispheric chart represented by said polar coordinates to obtain a current vector (assumed as A(r, θ, t)) from said magnetocardiogram data corresponding to said coordinate point (r, θ, t) by an arithmetic processing, thereby displaying said planispheric chart that represents distribution of said A (r, θ, t) on said display device.

13. The biomagnetic measurement apparatus according to claim 12,
    wherein a change of distribution of said A (r, θ, t) is displayed on said planispheric chart on said display device.

14. The biomagnetic measurement apparatus according to claim 12,
    wherein a change of distribution of said A (r, θ, t) in any of time bands in which P, QRS, and T waves of said magnetocardiogram are generated is displayed on said planispheric chart on said display device.

15. The biomagnetic measurement apparatus according to claim 12,
wherein said arithmetic processing unit is used to perform a processing to obtain the maximum value max $\{A(r, \theta, t)\}$ or average value $<\{A(r, \theta, t)\}>$ of said $A(r, \theta, t)$ on said radius vector r at said point of time t and at said oblique angle θ of said A (r,θ,t) to assume B(θ, t)=max $\{A(r, \theta, t)$ or $B(\theta, t)=<\{A(r, \theta, t)\}>$ so that said B (θ, t) is displayed on said display device by assuming both of said point of time t and said oblique angle θ as two axes.

16. The biomagnetic measurement apparatus according to claim 15,
wherein said arithmetic processing device is used to perform a processing to obtain the maximum value max of said B (θ, t) and said maximum value is displayed on said display device.

17. The biomagnetic measurement apparatus according to claim 12,
wherein said first and second magnetocardiogram data are displayed on said display device.

18. The biomagnetic measurement apparatus according to claim 12,
wherein a contour line that links points having a same Td (r, θ) defined as Td (r, θ)=0 is displayed on said planispheric chart on said display device in case |A(r, θ, t=[t0, t1])|≧Athr is satisfied while any of said time bands in which P, QRS, and T waves of said magnetocardiogram waveforms are generated is assumed as [t0, t1], the absolute value of said A(r, θ, t=[t0, t1]) at [t0, t1] is assumed as |A(r, θ, t=[t0, t1])|, and a predetermined threshold value is assumed as Athr, as well as in case |A(r, θ, t)=[t0, t1])|<Athr is satisfied and Td(r,θ)=tmax is satisfied while a predetermined threshold value is assumed as Athr, Td (r, θ)=tmax and a point of time t at which the maximum value of $\{A(r, \theta, t=[t0, t1])|$ is obtained is assumed as tmax.

19. The biomagnetic measurement apparatus according to claim 18,
wherein said coordinate point at which the maximum value of said Td (r, θ) is obtained is displayed on said display device together with said maximum value.

20. The biomagnetic measurement apparatus according to claim 12,
wherein a contour line that links points having said same Td (r, θ) defined as Td (r, θ)=0 is displayed on said planispheric chart on said display device while said contour line is projected on the surface of a 3-dimensional heart model in case |A(r, θ, t=[t0, t1])|≧A thr is satisfied while any of said time bands in which P, QRS, and T waves of said magnetocardiogram waveforms are generated is assumed as [t0, t1], the absolute value of said A(r, θ, t=[t0, t1]) at [t0, t1] is assumed as |A(r, θ, t=[t0, t1])|, and a predetermined threshold value is assumed as Athr, as well as in case |A(r, θ, t)=[t0, t1])|<A thr is satisfied and Td(r,θ)=tmax is satisfied while a predetermined threshold value is assumed as A thr, Td(r, θ)=tmax and a point of time t at which the maximum value of $\{A(r, \theta, t=[t0, t1])|$ is obtained is assumed as tmax.

21. The biomagnetic measurement apparatus according to claim 20,
wherein said coordinate point at which the maximum value of said Td (r, θ) is obtained is displayed on said display device together with said maximum value.

22. The biomagnetic measurement apparatus according to claim 12,
wherein all of said first to third magnetic field data are disposed at equal intervals on said radius vector r and at said oblique angle θ.

* * * * *